(12) United States Patent
Mathiowitz et al.

(10) Patent No.: US 8,486,438 B2
(45) Date of Patent: Jul. 16, 2013

(54) METHODS FOR PROGENITOR CELL RECRUITMENT AND ISOLATION

(75) Inventors: Edith Mathiowitz, Brookline, MA (US); Diana M. James, Providence, CT (US)

(73) Assignee: Brown University, Providence, RI (US)

( * ) Notice: Subject to any disclaimer, the term of this patent is extended or adjusted under 35 U.S.C. 154(b) by 1210 days.

(21) Appl. No.: 10/587,884

(22) PCT Filed: May 17, 2004

(86) PCT No.: PCT/US2004/015443
§ 371 (c)(1),
(2), (4) Date: Jun. 5, 2007

(87) PCT Pub. No.: WO2005/074836
PCT Pub. Date: Aug. 18, 2005

(65) Prior Publication Data
US 2009/0022777 A1    Jan. 22, 2009

Related U.S. Application Data

(60) Provisional application No. 60/539,596, filed on Jan. 29, 2004.

(51) Int. Cl.
*A61K 9/70* (2006.01)
*A61K 38/19* (2006.01)
*C07K 14/52* (2006.01)
*A61F 2/00* (2006.01)

(52) U.S. Cl.
USPC ............. 424/425; 424/486; 424/499; 514/7.6

(58) Field of Classification Search
USPC ........................ 424/425, 486, 499; 514/7.6
See application file for complete search history.

(56) References Cited

U.S. PATENT DOCUMENTS

| | | | |
|---|---|---|---|
| 3,266,987 A | 8/1966 | Crowley et al. | |
| 4,460,563 A | 7/1984 | Calanchi | |
| 4,794,000 A | 12/1988 | Ecanow | |
| 5,019,400 A | 5/1991 | Gombotz et al. | |
| 5,916,554 A * | 6/1999 | Dionne et al. | 424/93.21 |
| 6,131,211 A | 10/2000 | Hennessey | |
| 6,235,224 B1 | 5/2001 | Mathiowitz et al. | |
| 6,340,588 B1 | 1/2002 | Nova et al. | |
| 2003/0007954 A1 | 1/2003 | Naughton et al. | |
| 2003/0082148 A1 * | 5/2003 | Ludwig et al. | 424/93.7 |

FOREIGN PATENT DOCUMENTS
WO    WO03040336 A2 *    5/2003

OTHER PUBLICATIONS

Asahara et al., Isolation of putative progenitor endothelial cells for angiogenesis. Science. Feb. 14, 1997;275(5302):964-7. Abstract Only.
Asahara et al., VEGF contributes to postnatal neovascularization by mobilizing bone marrow-derived endothelial progenitor cells. EMBO J. Jul. 15, 1999;18(14):3964-72.
Bautz et al., Expression and secretion of vascular endothelial growth factor-A by cytokine-stimulated hematopoietic progenitor cells. Possible role in the hematopoietic microenvironment. Exp Hematol. Jun. 2000;28(6):700-6. Abstract Only.
Edelberg et al., Young adult bone marrow-derived endothelial precursor cells restore aging-impaired cardiac angiogenic function. Circ Res. May 31, 2002;90(10):E89-93.
Egilmez et al., Cytokines delivered by biodegradable microspheres promote effective suppression of human tumors by human peripheral blood lymphocytes in the SCID-Winn model. J Immunother (1997). Mar.-Apr. 2000;23(2):190-5. Abstract Only.
Handgretinger et al., Biology and plasticity of CD133+ hematopoietic stem cells. Ann N Y Acad Sci. May 2003;996:141-51. Abstract Only.
Hattori et al., Vascular endothelial growth factor and angiopoietin-1 stimulate postnatal hematopoiesis by recruitment of vasculogenic and hematopoietic stem cells. J Exp Med. May 7, 2001;193(9):1005-14.
Heissig et al., Recruitment of stem and progenitor cells from the bone marrow niche requires MMP-9 mediated release of kit-ligand. Cell. May 31, 2002;109(5):625-37. Abstract Only.
Hill et al., Cancer immunotherapy with interleukin 12 and granulocyte-macrophage colony-stimulating factor-encapsulated microspheres: coinduction of innate and adaptive antitumor immunity and cure of disseminated disease. Cancer Res. Dec. 15, 2002;62(24):7254-63.
Kalka et al., Transplantation of ex vivo expanded endothelial progenitor cells for therapeutic neovascularization. Proc Natl Acad Sci U S A. Mar. 28, 2000;97(7):3422-7.
Kalka et al., Vascular endothelial growth factor(165) gene transfer augments circulating endothelial progenitor cells in human subjects. Circ Res. Jun. 23, 2000;86(12):1198-202.
Kreitz et al., Controlled delivery of therapeutics from microporous membranes. II. In vitro degradation and release of heparin-loaded poly(D,L-lactide-co-glycolide). Biomaterials. Dec. 1997;18(24):1645-51. Abstract Only.
Kreitz et al., Controlled delivery of therapeutics from microporous membranes. I. Fabrication and characterization of microporous polyurethane membranes containing polymeric microspheres. Biomaterials. Apr. 1997;18(8):597-603. Abstract Only.
Luttun et al., Vascular progenitors: from biology to treatment. Trends Cardiovasc Med. Feb. 2002;12(2):88-96. Abstract Only.
Lyden et al., Impaired recruitment of bone-marrow-derived endothelial and hematopoietic precursor cells blocks tumor angiogenesis and growth. Nat Med. Nov. 2001;7(11):1194-201.
Mathiowitz et al., Biologically erodable microspheres as potential oral drug delivery systems. Nature. Mar. 27, 1997;386(6623):410-4. Abstract Only.
Murayama et al., Determination of bone marrow-derived endothelial progenitor cell significance in angiogenic growth factor-induced neovascularization in vivo. Exp Hematol. Aug. 2002;30(8):967-72. Abstract Only.

(Continued)

*Primary Examiner* — Taeyoon Kim
(74) *Attorney, Agent, or Firm* — Pabst Patent Group LLP

(57) ABSTRACT

The invention relates to the use of one or more growth factors in a drug delivery system, optionally with an external mesh housing, to recruit and optionally harvest progenitor cells. These cells include those that normally reside in the bone marrow.

20 Claims, 14 Drawing Sheets

OTHER PUBLICATIONS

Murohara et al., Transplanted cord blood-derived endothelial precursor cells augment postnatal neovascularization. J Clin Invest. Jun. 2000;105(11):1527-36.

Padovan et al., Expression of neuronal markers in differentiated marrow stromal cells and CD133+ stem-like cells. Cell Transplant. 2003;12(8):839-48. Abstract Only.

Peichev et al., Expression of VEGFR-2 and AC133 by circulating human CD34(+) cells identifies a population of functional endothelial precursors. Blood. Feb. 1, 2000;95(3):952-8. Abstract Only.

Rafii et al., Therapeutic stem and progenitor cell transplantation for organ vascularization and regeneration. Nat Med. Jun. 2003;9(6):702-12.

Rafii et al., Characterization of hematopoietic cells arising on the textured surface of left ventricular assist devices. Ann Thorac Surg. Dec. 1995;60(6):1627-32.

Rafii et al., Efficient mobilization and recruitment of marrow-derived endothelial and hematopoietic stem cells by adenoviral vectors expressing angiogenic factors. Gene Ther. May 2002;9(10):631-41.

Sandor et al., Transfection of HEK cells via DNA-loaded PLGA and P(FASA) nanospheres. J Drug Target. Sep. 2002;10(6):497-506. Abstract Only.

Sandor et al., Effect of protein molecular weight on release from micron-sized PLGA microspheres. J Control Release. Oct. 19, 2001;76(3):297-311. Abstract Only.

Shi et al., Evidence for circulating bone marrow-derived endothelial cells. Blood. Jul. 15, 1998;92(2):362-7.

Takahashi et al., Ischemia- and cytokine-induced mobilization of bone marrow-derived endothelial progenitor cells for neovascularization. Nat Med. Apr. 1999;5(4):434-8.

Tamaki et al., Engraftment of sorted/expanded human central nervous system stem cells from fetal brain. J Neurosci Res. Sep. 15, 2002;69(6):976-86. Abstract Only.

Tateishi-Yuyama et al., Therapeutic angiogenesis for patients with limb ischaemia by autologous transplantation of bone-marrow cells: a pilot study and a randomised controlled trial. Lancet. Aug. 10, 2002;360(9331):427-35.

Young et al., VEGF increases engraftment of bone marrow-derived endothelial progenitor cells (EPCs) into vasculature of newborn murine recipients. Proc Natl Acad Sci U S A. Sep. 3, 2002;99(18):11951-6. Epub Aug. 23, 2002.

* cited by examiner

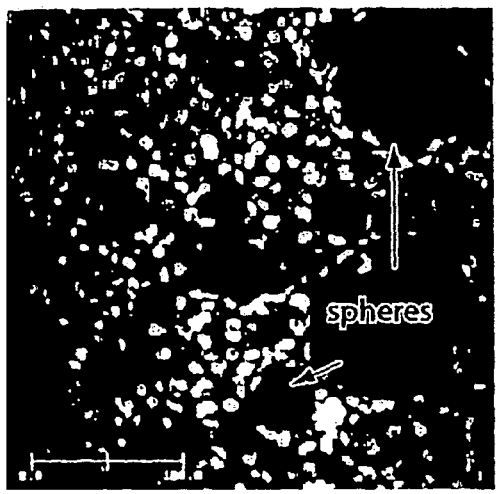 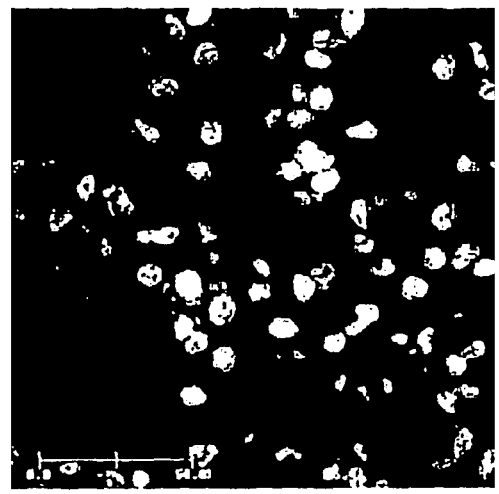
Fig. 12A          Fig. 12B
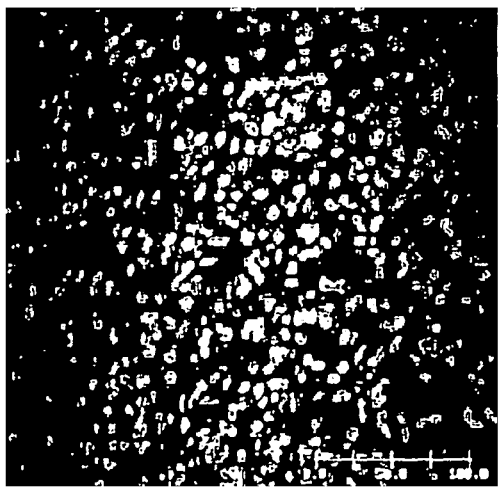 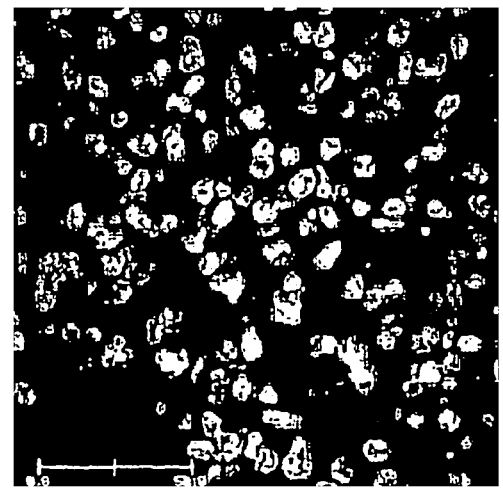
Fig. 13A          Fig. 13B

METHODS FOR PROGENITOR CELL RECRUITMENT AND ISOLATION

RELATED APPLICATIONS

This application is a national stage filing under 35 U.S.C. §371 of international application PCT/US2004/015443, filed 17 May 2004, which was published under PCT Article 21(2) in English, which claims priority to U.S. Provisional Patent Application Ser. No. 60/539,596, filed Jan. 29, 2004 entitled "BONE MARROW PROGENITOR CELL RECRUITMENT TO AN ECTOPIC MESH IMPLANT USING CONTROLLED RELEASE OF CYTOKINES AND GROWTH FACTORS", the contents of both of which are incorporated by reference herein in their entirety.

FIELD OF THE INVENTION

The invention relates to mobilization, recruitment and optionally harvest and isolation of progenitor cells in a subject.

BACKGROUND OF THE INVENTION

In the last 5-10 years there has been numerous data to suggest the presence of endothelial progenitor cells (EPCs) that can be recruited from the bone marrow in adult animals and in humans (Rafii and Lyden, Nat Med, 2003. 9(6):702-12). Several papers have strongly suggested the therapeutic potential of these cells. For example, Murohara, et al., and Kalka et al., have reported that infusion of selected populations of cells from the bone marrow in animals improves angiogenesis in ischemic limbs (Murohara et al., J Clin Invest, 2000. 105(11):1527-36; Kalka et al., PNAS, 2000. 97(7):3422-3427). Furthermore, Dacron grafts implanted in dogs were reportedly endothelialized exclusively by cells from transplanted bone marrow (Shi et al., Blood, 1998. 92(2):362-7). Two studies reported in humans have also been significant. Left ventricular assist devices (LVADs) removed after 6 months were reported to be colonized by CD34+ and VEGFR2+ endothelial and hematopoietic cells, both markers for early progenitor cells (Rafii et al., Ann Thorac Surg, 1995. 60(6):1627-32). In addition, autologous transplantation of bone marrow cells reportedly improved patient peripheral vascular disease (Tateishi-Yuyama et al., Lancet, 2002. 360 (9331):427-35). Thus, this cell population exists in the bone marrow and can improve significant pathophysiological cardiovascular conditions, according to these studies.

These and other animal studies have experimented with the vasculogenic potential of bone marrow by either delivering whole bone marrow transplants or selected cell populations via intravenous or intramuscular administration (Tateishi-Yuyama et al., Lancet, 2002. 360(9331):427-35; Edelberg et al., Circ Res, 2002. 90(10):E89-93; Heissig et al., Cell, 2002. 109(5):625-37; Young et al., Proc Natl Acad Sci, 2002. 99(18):11951-6; Murayama et al., Exp. Hematol, 2002. 30(8):967-72). These bone marrow derived EPCs appear to be attracted to angiogenic foci in the peripheral vasculature (Edelberg et al., Circ Res, 2002. 90(10):E89-93; Lyden et al., Nature and Medicine, 2001. 7:1194-1201). Recent work has reported the ability to mobilize and recruit these cells using adenoviral vectors expressing angiogenic factors and recombinant proteins like VEGF, angiopoietin 1 and stromal derived factor-1 into the bloodstream (Rafii et al., Gene Therapy, 2002. 9:631-641; Hattori et al., J. Exp. Med., 2001. 193(9):1005-1014). Others have also examined the factors that govern the recruitment of endothelial progenitor cells (Kalka et al., PNAS, 2000. 97(7):3422-3427; Asahara et al., Science, 1997. 275(5302):964-7; Asahara et al., EMBO, 1999. 18(14):3964-3972).

SUMMARY OF THE INVENTION

The invention relates broadly to the use of one or more growth factors (including cytokines) to mobilize and recruit progenitor cells to particular regions in the body. This is useful in regeneration or repair of particular tissues. Additionally, it facilitates the isolation of progenitor cells preferably prior to further lineage commitment or differentiation. Such isolated progenitor cells can be harvested from the subject at these specific regions and used in vitro or re-implanted in the same or a different subject.

In one aspect, the invention provides a method for isolating progenitor cells from a subject, comprising introducing into a subject an implant that comprises an angiogenic/vasculogenic factor and a bone marrow recruiting factor, allowing sufficient time for progenitor cells to migrate to the implant, and removing the implant from the subject.

In another aspect, the invention provides a method for isolating progenitor cells from a subject, comprising introducing into a subject an implant that comprises at least one growth factor, allowing sufficient time for progenitor cells to migrate to the implant, and removing the implant from the subject. In another embodiment, the at least one growth factor is an angiogenic/vasculogenic factor such as but not limited to VEGF. In another embodiment, the at least one growth factor is a bone marrow recruiting factor. In one embodiment, the at least one growth factor is two growth factors. In a related embodiment, the two growth factors are an angiogenic/vasculogenic factor and a bone marrow recruiting factor.

In another aspect, the invention provides a method of recruiting progenitor cells to a bodily site in a subject, comprising introducing in a bodily site of a subject an implant that comprises an angiogenic/vasculogenic factor and a bone marrow recruiting factor, and allowing sufficient time for progenitor cells to migrate to the implant, wherein neither factor is bound to the implant. In an important embodiment, the implant is not a scaffold upon which cells bind and grow. Rather, the implant provides growth factor regardless and preferably without cell attachment and growth thereto.

In one embodiment, the bodily site is remote from the vasculature. In another embodiment, the implant is comprised in a vascular prosthesis. In another embodiment, the bodily site is myocardium, vasculature, skin, peritoneum, muscle, pericardium, central nervous system, peripheral nervous system, cranium, gastrointestinal tract, liver, respiratory tissue, lung, kidney, stomach, esophagus, mouth, throat or spine.

Various embodiments can be equally applied to the foregoing aspects. These are recited below.

The progenitor cells may be but are not limited to endothelial progenitor cells, hematopoietic progenitor cells, hemangioblasts, neural progenitor cells or epithelial progenitor cells. In one embodiment, the progenitor cells are $CD133^+$. In another embodiment, the progenitor cells are CD34+.

In important embodiments, the subject is a human.

In one embodiment, the implant comprises a drug delivery system. In a related embodiment, the drug delivery system comprises a plurality of microspheres, microparticles, nanospheres, macrospheres, nanoparticles, macroparticles, matrices, beads, films, rods, coatings or hydrogels. In one embodiment, a first subset of the plurality comprises an angiogenic/vasculogenic factor and a second subset of the plurality comprises a bone marrow recruiting factor. In another embodiment, at least a subset of the plurality comprises both an angiogenic/vasculogenic factor and a bone marrow recruiting factor. In one embodiment, the drug delivery system is prepared using phase inversion nanoencapsulation (PIN).

In one embodiment, the drug delivery system is contained in a mesh housing which is preferably non-biodegradable (at least not significantly biodegradable during implant time if the implant is to be harvested).

In another embodiment, the implant comprises a polymer. In some embodiments, the polymer is biodegradable. The polymer may be a polyanhydride. The polymer may also be a poly-L-lactide (PLA), PLGA, a poly(fumaric acid:sebacic acid) or polycaprolactone.

In one embodiment, the angiogenic/vasculogenic factor is VEGF-A, VEGF-B, VEGF-C, VEGF-D, VEGF-E, aFGF, bFGF, angiopoietin-1, angiopoietin-2, angiogenin, Del-1, follistatin, HGF/SF, leptin, midkine, PLGF, PD-ECGF, PDGF-BB, PTN, progranulin, proliferin, TGF-alpha, TGF-beta, TNF-alpha, IGF-1 or IGF-2. In an important embodiment, the angiogenic/vasculogenic factor is a VEGF, such as but not limited to rhVEGF$_{165}$.

In another embodiment, the bone marrow recruiting factor is GM-CSF, G-CSF, SDF-1α, SDF-1β, MCP-1, stem cell factor/kit ligand, M-CSF, IL-8, SF20 or HCC-1. In some embodiments, the bone marrow recruiting factor is GM-CSF. In important embodiments, the angiogenic/vasculogenic growth factor is a VEGF and the bone marrow recruiting factor is GM-CSF.

In one embodiment, the implant is introduced into the subject intravascularly, subcutaneously, intrademially, intraperitoneally, intramuscularly, intrapericardially, intracranially, gastrointestinally, intra-liver, intra-lung, buccal, intra-kidney, intra-stomach, esophageally, intrathecally and intraspinal.

In one embodiment, the time for progenitor cells to migrate to the implant is at least 7 days, at least 14 days, at least 21 days, or at least 28 days.

In one embodiment, to migrate to the implant comprises adhering to the implant. In another embodiment, to migrate to the implant comprises entering the implant.

In one embodiment, the methods further comprises isolating the progenitor cells from the implant and/or culturing the progenitor cells.

In another embodiment, the methods further comprise re-introducing the progenitor cells into a recipient subject. In a related embodiment, the progenitor cells are re-introduced into the recipient subject after the recipient subject has undergone chemotherapy, radiation, balloon angioplasty, cosmetic surgery, cardiac surgery, myocardial infarction, transient ischemic attack or ischemia. In another embodiment, the progenitor cells are re-introduced into the recipient subject that has a neurodegenerative disease such as but not limited to Alzheimer's disease, Parkinson's disease, ALS or MS. In one embodiment, the subject and the recipient subject are the same. In another embodiment, the subject and the recipient subject are allogeneic.

These and other aspects and embodiments will be described in greater detail herein.

BRIEF DESCRIPTION OF THE DRAWINGS

FIG. 12A is a representative confocal scanning image of a cross-section taken from all animal implanted with 2% BSA spheres (M10). No CD133+ cells were found within or external to the implant. (Original magnification 40×.)

FIG. 12B is a close-up confocal scanning image of a cross-section taken from an animal implanted with 2% BSA spheres (M10) showing dapi-stained nuclei (blue). No CD133+ cells are present. (Original magnification 80×.)

FIG. 13A is a representative confocal image of a cross-section taken from an animal implanted with a nylon mesh loaded with GM-CSF microspheres (M2). Some CD133+ cells (punctate red staining) were found dispersed throughout the implant. (Original magnification 40×.)

FIG. 13B is a close-up confocal image of a cross-section taken from an animal implanted with a nylon mesh loaded with GM-CSF microspheres (M2) showing dapi-stained nuclei (blue) and some CD133+ cells (red). (Original magnification 80×.)

Figure 1:
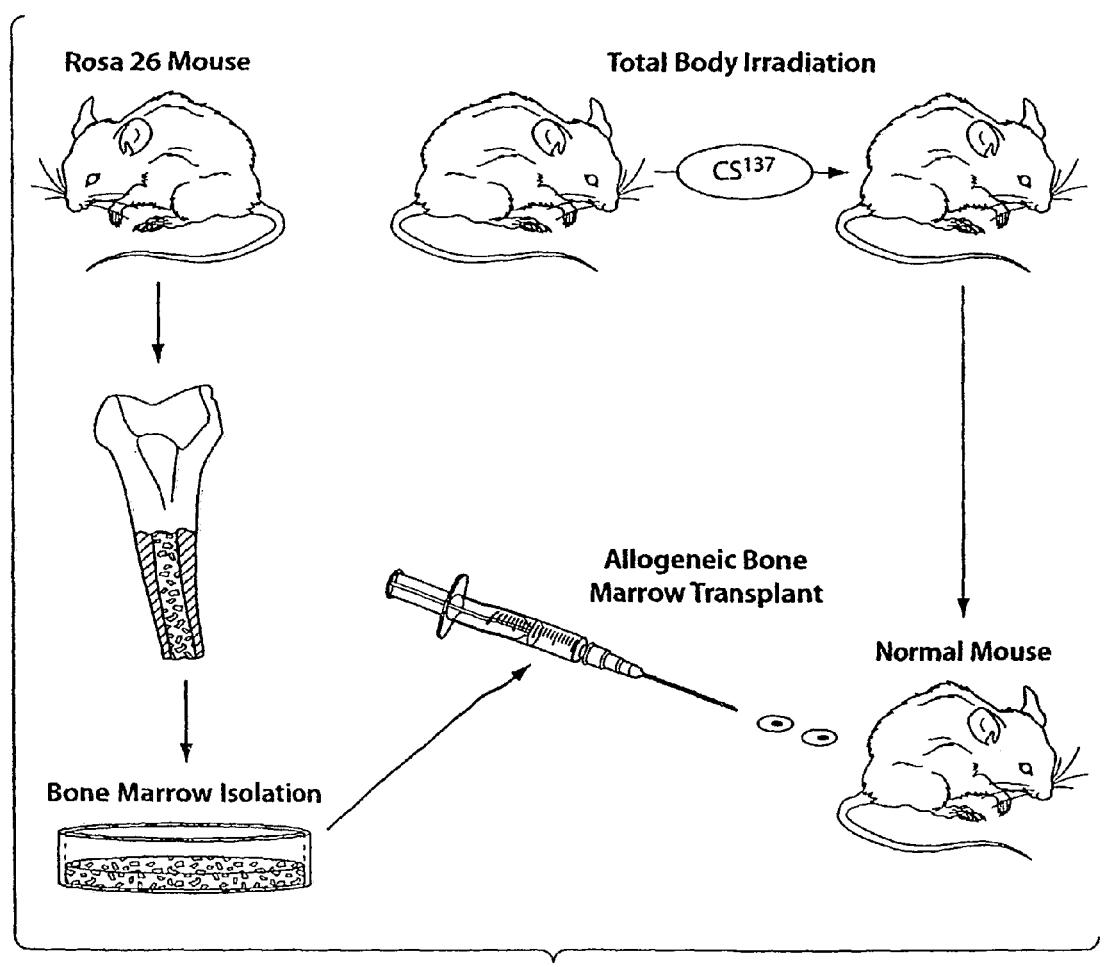
FIG. 1 is a schematic showing the experimental procedure for some of the Examples. Bone marrow isolated from Rosa26 mice genetically modified to contain the bacterial lacz gene was collected and injected into age-matched, strain-matched "normal" mice via the tail vein. These normal mice underwent total body irradiation to remove endogenous bone marrow prior to the transplant.

It is to be understood that the Figures are not required for enablement of the invention.

DETAILED DESCRIPTION OF THE INVENTION

The invention relates in its broadest sense to methods and compositions useful for recruitment of cells, preferably progenitor cells, to particular sites in the body. Cells are generally recruited using implants that comprise one or more growth factors. The ability to recruit cells to particular sites within a subject facilitates tissue repair and/or reconstruction that may be necessary as a result of, for example, genetic abnormality (e.g., hereditary disease), diseases such as heart disease, infections, necroses, trauma and external stresses such as wounds (e.g., surgical wounds).

In a further aspect, the invention also provides for the isolation (e.g., capture and harvest) of cells, preferably progenitor cells, from the body. These cells can be used for a multitude of applications including re-infusion into the same or a different subject, optionally after ex vivo manipulation. The ability to recruit specifically particular cells to a removable implant in a subject substantially reduces the need to further purify the cells ex vivo. This aspect of the invention also the dependence on embryonic stem cells as a source of progenitor cells for tissue repair and regeneration in vivo, since it uses adult progenitor cells from the same or a different subject instead.

The invention is based in part on the finding that the bone marrow reservoir of progenitor cells (such as but not limited to endothelial progenitor cells) can be mobilized (and thus captured) through the controlled release of one or more growth factors. This provides therapeutic options that could significantly improve, for example, cardiovascular repair. The Examples demonstrate that drug delivery systems delivering intact, bioactive molecules such as growth factors in a localized, specific space can recruit progenitor cells from the bone marrow to an ectopic site or implant, thereby allowing for retrieval (i.e., harvest) of such cells from the body.

These findings are based on experiments using normal 7-8 week old B6;129S mice that underwent sub-lethal total body irradiation and then received a bone marrow transplant of $10 \times 10^6$ bone marrow cells containing the bacterial lacz gene (bone marrow cells harvested from Rosa26 mice on a background of B6129S). Replacement of normal host bone marrow by lacz$^+$ marked bone marrow was confirmed after 8 weeks using flow cytometry analysis. Nine weeks post-transplantation, nylon mesh implants containing microspheres loaded with appropriate growth factors were implanted into the dorsal subcutaneous space. Controls per time point included empty nylon mesh (n=2), mesh and BSA control spheres (n=3), and mesh and total theoretical dose delivered from microspheres of VEGF and GM-CSF (plain protein) (n=3). Experimental groups per time point included mesh and 0.1% VEGF loaded spheres (n=3), mesh and 0.2% GM-CSF loaded spheres (n=3), and mesh and 0.1% VEGF loaded spheres and 0.2% GM-CSF loaded spheres (n=3). After 3 days, 7 days, 14 days and 21 days, animals were sacrificed, and implants and adjacent tissue were removed and processed for histological analysis. Marked recruitment of lacz$^+$ cells to implants containing both VEGF and GM-CSF loaded microspheres was observed. Cell recruitment was specific to this implant and was not seen to the same extent in any other group studied, although VEGF loaded microspheres could induce some recruitment when used alone. Remarkably, recruited lacz+ cells were "captured" entirely inside the mesh implant and could easily be removed for further analysis or culture.

Three main approaches have thus far been documented and explored in the literature to acquire or recruit endothelial progenitor cells in an adult animal, however, each approach is somewhat limited in its application to humans in a clinical setting. These cells can either be selected using fluorescence-activated cell sorting with markers specific to progenitor cells from the bone marrow itself, isolated using the same technique from the bloodstream after exposing the animal to systemic recruiting factors, or recruited to a peripheral site after sequential administration of exogenous cytokines. The first two methods could involve a specifically selected cellular transplant to a patient, which would require the co-administration of immunosuppressive agents since the cells are known to contain classical MHC I and MHC II molecules. The third approach would involve at least daily administration of the appropriate cytokine to achieve the desired therapeutic effect since these cytokines have very short half-lives in the bloodstream.

The present invention is not necessarily dependent upon further purification of progenitor cells since the recruited population will be enriched in progenitor cells. The present invention also does not require repeated administration of growth factors to a subject since it provides for factor release in a sustained and controlled, steady fashion. The efficacy of sustained and/or controlled release drug delivery systems has been demonstrated previously (Hill et al., Cancer Res., 2002. 62(24):7254-63; Egilmez et al., J. Immunother, 2000. 23(2): 190-5).

The invention uses an implant to administer one or more growth factors in a subject. The implant comprises a drug delivery system and may also comprise a housing for such a drug delivery system. As used herein, a drug delivery system is a physical entity that releases one or more drugs into a subject over time. As used herein, the terms implant and drug delivery system specifically exclude mechanical entities such as pumps. In other embodiments, the drug delivery system is not intended to work as a scaffold for the growth of cells in vivo. The cells recruited to the implant need not contact the implant in order to regenerate or repair damages tissues, for example.

In some aspects, the implant further comprises an external porous housing such as but not limited to a mesh or sieve. The implant can be introduced into a subject and subsequently harvested from the subject. The external porous housing allows the migration of cells into, and subsequent capture in, the implant. Accordingly, the pores or openings in the external housing must be of a size to allow movement of cells, preferably progenitor cells, into the implant. The pore size will depend on the type of cell being recruited into the implant. Exemplary and non-limiting sizes include at least 1 micron, at least 5 microns, at least 10 microns, at least 20 microns, at least 30 microns, at least 40 microns, at least 50 microns, and the like. In some important embodiments, the pore size is about 15 microns to about 20 microns. The pores may be of regular or irregular shape. The pores may be generally circular although they are not so limited since it is possible for most cells to deform their shape into order to move into the implant.

The mesh can be made from virtually any material (including the polymers recited herein for the drug delivery systems) such as but not limited to metal, plastic (e.g., nylon), hydrogel, glass, and the like. Polymers particularly suited for use as the mesh component of the implants described herein include but are not limited to polyamides (e.g., nylon), polyesters, polypropylene, and fluorocarbons. The mesh can also comprise in whole or in part proteins, including naturally occurring proteins such as those recited herein. In order to increase the half-life of the protein and/or extend its biodegradation kinetics, it may be modified to make it less biodegradable. For example, the protein can be denatured by for example crosslinking using chemicals, heat and certain energy sources (as are known in the art). Mesh implants made from proteins may be formed and then exposed to crosslinking conditions prior to loading of the drug delivery system. Accordingly, the mesh may be biodegradable or non-biodegradable. If biodegradable, and if it is to be used to capture and harvest progenitor cells, then it preferably the mesh is made of materials having long degradation kinetics so that it is not significantly degraded during the implant time.

The drug delivery system may assume any conformation without limit. For example, it may be one or more nanospheres, microspheres, macrospheres, nanoparticles, microparticles, macroparticles, rods, fibers, films, gels, hydrogels, coatings, sheets, capsules, or a combination thereof. These may be solid or porous. It is to be understood that in some aspects of the invention (particularly those relating strictly to recruitment of progenitor cells), the drug delivery system (and its external housing) is not intended to be a scaffold upon which cells attach and grow. Rather, the drug delivery system need only release growth factor. Accordingly, it is not necessary that the growth factors be physically attached to the drug delivery system; they can be merely incorporated or encapsulated within the drug delivery system.

The size of spheres, particles, capsules and the like may vary depending upon the embodiment. In some instances, average particle size is between 10 nanometers and 10 micrometers, or between 10 nanometers and 5 micrometers, or between 10 nanometers and 2 micrometers, or between 10 nanometers and 1 micrometer, or between 10 and 100 nanometers. In some embodiments, the drug delivery system is a heterogeneous mixture of particles ranging in size from about 100 nm to about 1 micron. The particles can however be as large as 1 mm (or more), depending on the embodiment. Particle size may be much smaller than the pore size of the external housing (i.e., mesh housing) without loss of the particles, in some instances. This is because the particles are generally electrostatic and they prefer to aggregate with each other than to interact with for example a mesh made of nylon. As a result, the particles are less likely to exit the implant than would otherwise be expected given their size and that of the mesh pores.

As used herein the terms "microparticle" and "microencapsulation" are used broadly to refer to particles, spheres or capsules that have sizes on the order of millimeters, microns as well as nanometers. Thus, the terms "microparticle" "microsphere", "nanoparticle, "nanosphere", "nanocapsule" and "microcapsule" are used interchangeably.

Preferably, the drug delivery system is a polymer-based delivery system that releases the drug in preferably a controlled and/or sustained manner. Drug release is generally controlled by natural erosion of the polymer, with concomitant release of the drug contained therein, or by dissolution of the drug with bodily fluids regardless of the effect on the polymer. Techniques for making such polymer-based drug delivery systems are known Controlled delivery of various molecules ranging from small peptides, growth factors, drugs and nucleic acids has been described previously. Polymeric-based microspheres have been developed to deliver a variety of therapeutic molecules (Mathiowitz et al. Nature, 1997. 386:410-414; Sandor et al., J Drug Target, 2002. 10(6):497-506; Sandor et al., J Control Release, 2001. 76(3):297-311). In important embodiments, the growth factors are not bound to the drug delivery system.

The polymer may be biodegradable or non-biodegradable, provided it is at least biocompatible. As used herein, biodegradable means that a material such as a polymer can undergo degradation, decomposition, or physical or chemical breakdown once in vivo. The kinetics of biodegradation will vary depending upon the material used. As used herein, a biocompatible polymer is a polymer that does not produce an adverse or allergic immune response when introduced into a subject.

Examples of biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as copolymers. Preferred polymers for some embodiments include polyesters, polyanhydrides, polystyrenes and blends thereof. Particularly preferred polymers for some embodiments include polylactic acid, polyglycolic acid, and copolymers of lactic and glycoloic acid.

Examples of biocompatible polymers include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethylmethacrylate), poly(butylmethacrylate), poly(isobutyl-methacrylate), poly(hexlmethacrylate), poly (isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly (ethylene oxide), poly(ethylene terephthalate), poly(vinyl alcohols), poly(vinyl acetate, poly vinyl chloride and polystyrene.

Examples of synthetic water-soluble, biocompatible polymer include polyethylene oxide (PEO), polyvinyl alcohol, polyhydroxyethyl methacrylate, polyacrylamide, polyvinylpyrrolidone, polyethylene glycol, and combinations thereof.

Examples of biocompatible, biodegradable polymers include polyanhydrides, polyglycolic acid, polyhydroxy acids such as polylactic acid, polyglycolic acid and polylactic acid-glycolic acid copolymers, polyorthoesters, polyhydroxybutyrate, polyphosphazenes, polypropylfumerate, biodegradable polyurethanes, bone powder, hydroxyapatite, polyglycolide (PGA), copolymers of glycolide, glycolide/L-lactide copolymers (PGA/PLLA), lactide/trimethylene carbonate copolymers (PLA/TMC), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, copolymers of PLA, lactide/tetramethylglycolide copolymers, lactide/.alpha.-valerolactone copolymers, lactide/.alpha.-caprolactone copolymers, hyaluronic acid and its derivatives, polydepsipeptides, PLA/polyethylene oxide copolymers, unsymmetrical 3,6-substituted poly-1,4-dioxane-2,5-diones, poly-.beta.-hydroxybutyrate (PHBA), PHBA/.beta.-hydroxyvalerate copolymers (PHBA/HVA), poly-p-dioxanone (PDS), poly-.alpha.-valerlactone, poly-.beta.-caprolactone, methacrylate-N-vinyl-pyrrolidone copolymers, polyesteramides, polyesters of oxalic acid, polydihydropyranes, polyalkyl-2-cyanoacrylates, polyurethanes, polyvinylalcohol, polypeptides, poly-B-malic acid (PMLA), poly-B-alcanoic acids, polybutylene oxalate, polyethylene adipate, polyethylene carbonate, polybutylene carbonate, tyrosine based polycarbonates, and other polyesters containing silyl ethers, acetals, or ketals, alginates, and blends or other combinations of the aforementioned polymers.

Examples of naturally occurring water-soluble, biocompatible polymers include hyaluronic acid, chondroitin sulfate, carboxymethylcellulose, starch, zein, collagen, lecithin polyamino acids, chitosan, polysaccharides such as glycosaminoglycans, alginate, carageenan, and combinations thereof.

Examples of biocompatible, non-biodegradable polymers include polystyrenes, polyethylene vinyl acetates, polypropylenes, polymethacrylates, polyacrylates, polyethylenes, polyethylene oxides, glass (silica), polysilicates, polycarbonates, polytetrafluoroethylene, fluorocarbons, nylon, silicon rubber, stainless steel alloys, and combinations thereof.

Examples of non-biodegradable polymers include ethylene vinyl acetate, poly(meth) acrylic acid, polyamides, copolymers and mixtures thereof.

The drug delivery system when comprised of particles, spheres or capsules can be made in a number of ways. For example, microparticles may be prepared using any one of several common microencapsulation techniques. Different microencapsulation techniques produce a variety of microparticles having different properties under various conditions. Suitable methods of encapsulation may be selected to produce the desired physical and chemical properties of the encapsulant and the material to be encapsulated. Common microencapsulation techniques include but are not limited to spray drying, interfacial polymerization, hot melt encapsulation, phase separation encapsulation (solvent removal and solvent evaporation), spontaneous emulsion, solvent evaporation microencapsulation, solvent removal microencapsulation, coacervation, and low temperature microsphere formation and phase inversion nanoencapsulation (PIN). Each of these methods is well known in the art. A brief summary of the methods is presented below.

In spray drying, the core material to be encapsulated is dispersed or dissolved in a solution. Typically, the solution is aqueous and preferably the solution includes a polymer. The solution or dispersion is pumped through a micronizing nozzle driven by a flow of compressed gas, and the resulting aerosol is suspended in a heated cyclone of air, allowing the solvent to evaporate from the microdroplets. The solidified microparticles pass into a second chamber and are trapped in a collection flask.

Interfacial polycondensation is used to microencapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

In hot melt microencapsulation the core material (to be encapsulated) is added to molten polymer. This mixture is suspended as molten droplets in a nonsolvent for the polymer (often oil-based) which has been heated to approximately 10° C. above the melting point of the polymer. The emulsion is maintained through vigorous stirring while the nonsolvent bath is quickly cooled below the glass transition of the polymer, causing the molten droplets to solidify and entrap the core material.

In solvent evaporation microencapsulation, the polymer is typically dissolved in a water immiscible organic solvent and the material to be encapsulated is added to the polymer solution as a suspension or solution in organic solvent. An emulsion is formed by adding this suspension or solution to a beaker of vigorously stirring water (often containing a surface active agent to stabilize the emulsion). The organic solvent is evaporated while continuing to stir. Evaporation results in precipitation of the polymer, forming solid microcapsules containing core material.

The solvent evaporation process is designed to entrap a liquid core material in PLA, PLA/PGA copolymer, or PLA/PCL copolymer microcapsules. The PLA or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the PLA or copolymer to phase separate and migrate towards the surface of the core material droplets. This phase separated solution is then transferred into an agitated volume of nonsolvent, causing any remaining dissolved PLA or copolymer to precipitate and extracting any residual solvent from the formed membrane. The result is a microcapsule composed of PLA or copolymer shell with a core of liquid material.

In solvent removal microencapsulation, the polymer is typically dissolved in an oil miscible organic solvent and the material to be encapsulated is added to the polymer solution as a suspension or solution in organic solvent. An emulsion is formed by adding this suspension or solution to a beaker of vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid microcapsules containing core material.

In phase separation microencapsulation, the material to be encapsulated is dispersed in a polymer solution by stirring. While continuing to uniformly suspend the material through stirring, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the core material in a droplet with an outer polymer shell.

Spontaneous emulsification involves solidifying emulsified liquid polymer droplets by changing temperature, evaporating solvent, or adding chemical cross-linking agents. Physical and chemical properties of the encapsulant and the material to be encapsulated dictates the suitable methods of encapsulation. Factors such as hydrophobicity, molecular weight, chemical stability, and thermal stability affect encapsulation.

Encapsulation procedures for various substances using coacervation techniques have been described in the prior art, for example, in GB-B-929 406; GB-B-929 401; U.S. Pat. Nos. 3,266,987; 4,794,000 and 4,460,563. Coacervation is a process involving separation of colloidal solutions into two or more immiscible liquid layers (Ref. Dowben, R. General Physiology, Harper & Row, New York, 1969, pp. 142-143.).

Through the process of coacervation compositions comprised of two or more phases and known as coacervates may be produced. The ingredients that comprise the two phase coacervate system are present in both phases; however, the colloid rich phase has a greater concentration of the components than the colloid poor phase.

Components that may be used to formulate the coacervate system comprise anionic, cationic, amphoteric, and non-ionic surfactants. Anionic surfactants include di-(2 ethylhexyl) sodium sulfosuccinate; non-ionic surfactants include the fatty acids and the esters thereof; surfactants in the amphoteric group include (1) substances classified as simple, conjugated and derived proteins such as the albumins, gelatins, and glycoproteins, and (2) substances contained within the phospholipid classification, for example lecithin. The amine salts and the quaternary ammonium salts within the cationic group also comprise useful surfactants. Other surfactant compounds useful to form coacervates include compositions within the groups known as the polysaccharides and their derivatives, the mucopolysaccharides and the polysorbates and their derivatives. Synthetic polymers that may be used as surfactants include compositions such as polyethylene glycol and polypropylene glycol. Further examples of suitable compounds that may be utilized to prepare coacervate systems include glycoproteins, glycolipids, galactose, gelatins, modified fluid gelatins and galacturonic acid.

In addition, substances that are not intrinsically surface active may be used to prepare coacervates provided that they can be made so by chemical or other means. Fatty acids are not considered to be surface active compounds. However, when fatty acids are reacted with an alkaline chemical entity the resulting products will have surface-active properties.

Low temperature microsphere formation has been described, see, e.g., U.S. Pat. No. 5,019,400. The method is a process for preparing microspheres which involves the use of very cold temperatures to freeze polymer-biologically active agent mixtures into polymeric microspheres. The polymer is generally dissolved in a solvent together with an active agent that can be either dissolved in the solvent or dispersed in the solvent in the form of microparticles. The polymer/active agent mixture is atomized into a vessel containing a liquid non-solvent, alone or frozen and overlayed with a liquefied gas, at a temperature below the freezing point of the polymer/active agent solution. The cold liquefied gas or liquid immediately freezes the polymer droplets. As the droplets and non-solvent for the polymer is warmed, the solvent in the droplets thaws and is extracted into the non-solvent, resulting in hardened microspheres.

Another microencapsulating method is phase inversion nanoencapsulation (PIN). In PIN, a polymer is dissolved in an effective amount of a solvent. The agent to be encapsulated is also dissolved or dispersed in the effective amount of the solvent. The polymer, the agent and the solvent together form a mixture having a continuous phase, wherein the solvent is the continuous phase. The mixture is introduced into an effective amount of a nonsolvent to cause the spontaneous formation of the microencapsulated product, wherein the solvent and the nonsolvent are miscible. PIN has been described by Mathiowitz et al. in U.S. Pat. Nos. 6,131,211 and 6,235,224 that are incorporated herein by reference.

In some instances, it may be necessary to secure the implant in a particular bodily site. In these embodiments, therefore it may be preferable to use bioadhesive polymers. A bioadhesive polymer is one that binds to mucosal epithelium under normal physiological conditions. Bioadhesion in the gastrointestinal tract proceeds in two stages: (1) viscoelastic deformation at the point of contact of the synthetic material into the mucus substrate, and (2) formation of bonds between the adhesive synthetic material and the mucus or the epithelial cells. In general, adhesion of polymers to tissues may be achieved by (i) physical or mechanical bonds, (ii) primary or covalent chemical bonds, and/or (iii) secondary chemical bonds (i.e., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (i.e., Van der Waals interactions) and stronger specific interactions, which include hydrogen bonds. The hydrophilic functional groups primarily responsible for forming hydrogen bonds are the hydroxyl and the carboxylic groups. Numerous bioadhesive polymers are discussed in that application. Representative bioadhesive polymers of particular interest include bioerodible hydrogels described by A. S. Sawhney, C. P. Pathak and J. A. Hubell in Macromolecules. 1993, 26:581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly butylmethacrylate), poly(isobutylmethacrylate), poly(hexlmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). Most preferred is poly(fumaric-co-sebacic)acid.

Polymers with enhanced bioadhesive properties can be provided wherein anhydride monomers or oligomers are incorporated into the polymer. The oligomer excipients can be blended or incorporated into a wide range of hydrophilic and hydrophobic polymers including proteins, polysaccharides and synthetic biocompatible polymers. Anhydride oligomers may be combined with metal oxide particles to improve bioadhesion even more than with the organic additives alone. The incorporation of oligomer compounds into a wide range of different polymers, which are not normally bioadhesive, dramatically increases their adherence to tissue surfaces such as mucosal membranes.

The implants are introduced into subjects and maintained there for various periods of time depending upon their composition or the composition of their components. The kinetics will also depend upon the time required to recruit a sufficient number of progenitors into the bodily site or into the implant. In some embodiments, the time is at least 30 minutes, at least 1 hour, at least 2 hours, at least 4 hours, at least 6 hours, at least 12 hours, at least 18 hours or more. In some embodiments, the time is at least 1, at least 2, at least 3, at least 4, at least 5, at least 6 or at least 7 days. In others, it is at least one week, at least two weeks, at least three weeks, at least four weeks or more. In still other embodiments, it is at least one month, at least two months, or more. It is expected that different regions of the body will require different periods of time for recruitment and/or entry of progenitor cells into the implant. One of ordinary skill, based on the teachings provided herein, will be able to ascertain such times without undue experimentation.

The number of particles or spheres to be used in an implant will depend on the load of growth factor in each particle or sphere, the amount of growth factor that must be administered in vivo, and/or the size of implant (including external mesh housing) that will be tolerated by the subject. The number of particles or spheres may be as few as less than 10 to more than $10^9$. More preferably, there may be $10^3$-$10^9$ particles or spheres per implant.

The cells being recruited or isolated by the methods of the invention can be any cell type. In preferred embodiments, the cell is one capable of proliferation and even more preferably differentiation into one or more lineages. Thus, in some aspects, the cell is a progenitor cell. As used herein, a progenitor cell is a cell that is able to proliferate and which optionally may give rise to progeny of more than one lineage. Progenitor cells that are also able to self-renew are referred to herein as stem cell. Self-renewal is the ability of a cell to divide and give rise to at least one progeny that is identical to itself. It is in this way that stem cells are able to populate or maintain a cell population (such as hematopoietic cells) or an organ (such as a liver) throughout the lifespan of a subject. As used herein, progenitor cells include stem cells.

Examples of progenitors cells to be recruited or isolated according to the invention include but are not limited to hematopoietic progenitor cells, liver progenitor cells, neural progenitor cells (e.g., neural crest progenitor cells), embryonic progenitor cells, gonadal progenitor cells, mesenchymal progenitor cells (e.g., endothelial progenitor cells), mesodermal progenitor cells and myocardium progenitor cells.

Although not intending to be bound by any particular theory, it is contemplated that many if not all of these progenitor types can be derived from a tissue other than the one they eventually give rise to. It has been well accepted that the bone marrow contains hematopoietic stem cells (i.e., cells that can repopulate the entire hematopoietic system indefinitely). It is now also clear that the bone marrow also contains mesenchymal progenitor cells such as endothelial progenitor cells. These latter cells can be made to migrate away from the bone marrow and to a bodily site, for example, that is in need of endothelialization. Such sites include blood vessels that have been damaged (e.g., due to atherosclerosis, arteriolosclerosis, restenosis, and/or vascular surgery), bodily sites that are in need of blood flow (e.g., an ischemic tissue such as the brain or muscle), and the like.

It is also now emerging that progenitor cells of other types can also be found in the bone marrow. Whether such cells are indeed physically distinct from the previous progenitor cells, or whether they are the same cells but capable of differentiating into a multitude of lineages is not clear. The invention is not dependent on either mechanism; rather it simply takes advantage of these observations and provides a means for regenerating tissues of various types, relying primarily on the recruitment of progenitor cells from locations such as the bone marrow. As used herein, the progenitor cell type is named according to the type of tissue it is eventually used to repopulate rather than its source. For example, neural progenitor cell recruitment means that progenitor cells are made to migrate (or move) to a bodily site at which they can differentiate into neural cell types (e.g., neurons, glial cells, astrocytes, etc.)

Accordingly, the progenitor cells are generally defined operationally by, for example, the tissue which they eventually regenerate. Such cells can also be defined phenotypically by, for example, the cell surface marker(s) they express. Such markers are known in the art and include CD34 for hematopoietic progenitor cells and CD133 for endothelial progenitor cells and neural progenitor cells.

Table 1 lists current known markers for hematopoietic and endothelial progenitor and mature cells.

TABLE 1

| Marker | Present on cell types: | Description/Notes |
| --- | --- | --- |
| Lin⁻ | Not present on hematopoietic stem cells | Includes: glycophorin A, CD2, CD3, CD4, CD8, CD14, CD15, CD16, CD19, CD20, CD56, CD66b |
| CD34 | EPCs, ECs, stem and progenitor cells; Other mature cells | First differentiation marker of human hematopoietic stem cells; Present on 1-4% of bone marrow cells <1% of peripheral blood cells; To identify progenitor cells, usually purify via negative selection of another marker, e.g. CD38, CD33, CD71, HLA-DR, CD45RA |
| CD133/AC133 | EPCs, subset of stem cells Immature progenitors; Monocyte/granulocyte progenitors | Expressed on many (but not all) CD34$^+$ cells |
| CDCP1 | Similar to CD133 | Useful for enrichment of human HSCs and progenitor cells in conjunction with CD34 and CD133 |
| c-Kit/CD117 | HSCs, HPCs | Stem cell factor; Expressed on ⅔ of) CD34$^+$ cells; Not present on mature circulating blood cells |
| Sca-1 | HSCs in mice | |
| VEGFR-2/KDR (Flk-1) | EPCs, ECs, Subset of HSCs | Expressed on 0.1-0.5% of) CD34$^+$ cells in bone marrow; May be used in conjunction with CD34 to identify the "hemiangioblast" |
| VEGFR1 | HSCs, ECs | Expressed on 5% of CD34+ cells in human cord blood Stimulation promotes HSC proliferation |
| VE-cadherin | EPCs, ECs | Cell adhesion protein |
| AcLDL uptake | EPCs, ECs, HCs (*also some macrophages) | LDL uptake |
| CD31/PECAM-1 | EPCs, ECs, HCs | Adhesion molecule expressed on platelets, endothelial cells, leukocytes and their bone marrow precursors; Role in homophilic adhesion and heterophilic transendothelial migration |

TABLE 1-continued

| Marker | Present on cell types: | Description/Notes |
|---|---|---|
| vWF | EPCs, ECs, platelets, megakaryocytes | Mediates platelet adhesion to injured vessel walls<br>Serves as a carrier and stabilizer for coagulation factor VIII;<br>Synthesized by endothelial cells |
| Tie-2 | EPCs, ECs, HSCs, HPCs | Endothelial cell- specific receptor tyrosine kinase |

Abbreviations:
EPC = endothelial progenitor cell,
EC = endothelial cell,
HPC = hematopoietic progenitor cell,
HC = hematopoietic cell,
HSC = hematopoietic stem cell, The CD 133 marker is also used to identify neural progenitor cells. Tamaki, et al., using fluorescence activated cell sorting and human fetal brain tissue, identified a neural progenitor cell population based on CD133. These cells, under proper culturing conditions, formed "neurospheres," indicating their progenitor potential (Tamaki et al., J Neurosci Res., 2002. 69(6):976-86). The neurospheres can be used for a number of therapeutic uses. More recently, Padovan, et al., obtained human bone marrow stromal cells and showed CD133$^+$ cells expressed higher levels of neuronal marker proteins and acquired a neuronal morphology compared to CD133$^-$/CD34$^+$ cells (Padovan et al., Cell Transplant., 2003. 12(8):839-48).

As used herein, "recruiting progenitor cells" means to stimulate the movement of progenitor cells away from their normal location in the body to another location (including to an implant comprising a drug delivery system).

The drug delivery system comprises one or more growth factors. As used herein, a growth factor includes cytokines, interleukins, interferons, monokines, lymphokines, colony-stimulating factors, chemokines, etc. Two categories of growth factor are particularly important: angiogenic/vasculogenic factors and bone marrow recruiting factors. As used herein, angiogenic/vasculogenic factors are factors that stimulate angiogenesis and/or vasculogenesis. As used herein, bone marrow cell recruiting factors are factors that stimulate mobilization of bone marrow cells away from the bone and into for example peripheral blood. Although not intending to be bound by any particular theory, the invention contemplates that the drug delivery systems will be able to recruit cells into the general location in which the systems are located due to the factor(s) they release. Therefore, if the drug delivery system is implanted into the skin (e.g., intradermally), then it is expected that progenitor cells will migrate to that location in the skin.

Although not intending to be bound by any particular mechanism, it is possible to design drug delivery systems in which the bone marrow recruiting factor is released early in the implant time and the angiogenic/vasculogenic factor is released throughout the implant time. For example, it is possible to release the bone marrow recruiting factor in weeks 1 and 2 of a 5 week implant and to release the angiogenic/vasculogenic factor in weeks 2-5 or throughout the entire 5 weeks.

Table 2 lists examples of angiogenic and/or vasculogenic factors, and bone marrow recruiting factors. It is believed that a system designed to encourage the mobilization of endothelial progenitor cells from the bone marrow to an ectopic site will involve a combination of factors from each category.

TABLE 2

| Angiogenic and or Vasculogenic Factor | Bone Marrow Recruiting Factor (Chemokines/Cytokines) |
|---|---|
| Vascular endothelial growth factor (VEGF)/vascular permeability factor (VPF) (VEGF-A, VEGF-B, VEGF-C, VEGF-D, VEGF-E) | Granulocyte-monocyte colony-stimulating factor (GM-CSF) |
| Fibroblast growth factors: acidic (aFGF) and basic (bFGF) | Granulocyte colony-stimulating factor (G-CSF) |
| Angiopoietin-1 and Angiopoietin-2 | Stromal derived factor-1 alpha and beta |
| Angiogenin | Stem cell factor |
| Del-1 | Monocyte chemotactic protein-1 (MCP-1) |
| Follistatin | Soluble kit Ligand (sKitL) |
| Hepatocyte growth factor (HGF)/scatter factor (SF) | Monocyte colony stimulating factor (M-CSF) |
| Leptin | Interleukin-8 (IL-8) |
| Midkine | SF20 |
| Placental growth factor (PLGF) | HCC-1 |
| Platelet-derived endothelial cell growth factor (PD-ECGF) | |
| Platelet-derived growth factor-BB (PDGF-BB) | |
| Pleiotrophin (PTN) | |
| Progranulin | |
| Proliferin | |
| Transforming growth factor-alpha (TGF-alpha) | |
| Transforming growth factor-beta (TGF-beta) | |
| Tumor necrosis factor-alpha (TNF-alpha) | |
| Insulin-like growth factor-1 and -2 (IGF-1 and IGF-2) | |

VEGF exists in at least four forms as a result of alternative splicing of the VEGF gene (VEGF-121, VEGF-165, VEGF-189 and VEGF-206). Thus, VEGF may be selected from the group consisting of VEGF-A, VEGF-B, VEGF-C and VEGF-D. VEGF-A could be VEGF-A$_{165}$ or VEGF-A$_{121}$. VEGF-165 is the most predominant protein.

The invention is directed in some aspects to the treatment of subjects. As used herein, a subject shall mean a human or vertebrate mammal including but not limited to a dog, cat, horse, cow, pig, sheep, goat, or primate, e.g., monkey. As used herein, treatment includes preventing a disease or condition from occurring (e.g., in a subject predisposed to such a disease or condition but not manifesting any symptoms associated therewith); inhibiting a pre-existing disease or condition (e.g., either reducing the disease load or eliminating the disease altogether); and/or reducing or ameliorating symptoms associated with the disease or condition.

Diseases or conditions which the invention intends to treat include but are not limited to genetic conditions such as hereditary conditions (e.g., muscular dystrophy, cystic fibrosis, diabetes), conditions associated with external stress such as externally induced wounds, myointimal hyperplasia as a result of vascular surgery, balloon angioplasty or vascular stenting, hematopoietic deficiencies induced by radiation, chemotherapy, surgery, infections such as viral infections, bacterial infections, fungal infections, parasitic infections, prion-associated conditions, drugs such as antibiotics, autoimmune disorders such as lupus, and other conditions such as heart/coronary disease such as coronary occlusive disease, carotid occlusive disease, arterial occlusive disease, peripheral arterial disease, atherosclerosis, vasculitis, myocardial infarction, stroke, ischemia, thromboangiitis obliterans, thrombotic disorders, immune deficiency disorders, hemophilia, anemia, leukemia, neurodegenerative diseases, areas of ulceration including gastrointestinal ulcers, mouth ulcers and skin ulcers, areas of necrosis such as ischemic tissue, deep rooted infections such as deep muscle infections, bone infections (associated with prostheses), and the like.

Neurodegenerative diseases include Parkinson's disease, Parkinsonian disorders, Huntington's disease, Alzheimer's disease, Amyotrophic Lateral Sclerosis (ALS), spinal ischemia, ischemic stroke, spinal cord injury, cancer-related brain/spinal cord injury, cerebral palsy, epilepsy, multiple sclerosis, and the like. Other neural disorders include psychiatric disorders believed to have a somatic basis such as but not limited to schizophrenia, phobias, bipolar disorders, psychoses, depression, anxiety syndromes, obsessive compulsive disorder, dementia, narcolepsy, attention deficit disorder, autism, and the like.

The invention can be applied to any condition or disease which would benefit from an augmentation in vascularization. Such conditions or diseases include but are not limited to myocardial infarction, peripheral vascular disease, diabetic ulcers, ischemic bowel disease, ischemic conditions such as but not limited to transient ischemic attacks (e.g. stroke), endothelialization of biomaterial surfaces such as vascular grafts and left ventricular assist devices (LVAD), atherosclerosis, hypertension, tachycardia and arrhythmia.

The invention can also be applied to any condition or disease which would benefit from tissue repair or regeneration (in whole or in part). Such conditions or diseases include but are not limited to artificial skin grafting (for example in burn victims or bed-ridden subjects that develop bed sores or ulcers), vascular grafting such as small vessel grafting, stent implantation such as vascular stent implantation, and ischemic conditions.

The invention, as it relates to recruitment and harvest of progenitor cells, can be further applied to conditions that affect tissues such as cardiovascular tissue, gastrointestinal tissue (such as gastrointestinal epithelium), pulmonary tissue, musculoskeletal tissue, neurologic tissue, endocrine tissue, hematologic tissue, and the like.

The invention can also be applied to subjects undergoing cell-ablative therapies. As an example, cancer patients undergoing radiation or chemotherapy can have their progenitor cells collected prior to such therapies and then re-introduced into them following the therapy. Preferably, the cancer is not a leukemia or other bone marrow residing cancer. Additionally, the invention can be used to recruit cells of the immune system to a permissive microenvironment in which the body's own immune system could be stimulated and enhanced to fight either cancer or infections such as HIV infection.

The progenitor cells recruited into the implant or into the vicinity of the drug delivery system can be used to regenerate or repair a tissue in the same or a different subject. If the recruited progenitor cells are not harvested, then they will be used to regenerate or repair a tissue in the vicinity of the drug delivery system in the same subject. If instead they are harvested, they can be re-implanted (or re-infused, based on the route of administration) virtually anywhere in the body that is in need of such cells. They can be re-administered to the same subject but to a location different from that to which they were initially recruited. As an example, it may be easier to implant the drug delivery system in a more accessible site in the body such as the peritoneum or skin (and then harvest it) than to implant it in a less accessible site such as certain regions of the brain when for example what is desired is neural progenitor cell recruitment to such regions of the brain. They may also be used in a different subject, preferably a subject which will be (or can be made) tolerant of the cell transplant. This can be done either by selected histocompatible "donor" and "recipient" subjects, or immunosuppressing the recipient, for example. This can also be accomplished without significant external intervention for particular cell transplants. For example, some organ transplants are less dependent on complete or near complete histocompatibility between donor and recipient (e.g., kidney, where immunosuppressive therapies are able to circumvent the histo-incompatibility).

In still other embodiments, the invention contemplates harvest of progenitor cells from a subject, manipulation of the cells (such as for example ex vivo gene therapy) and then re-introducing the cells to the same subject, possibly at the same site of harvest. The invention also contemplates growth of harvested ex vivo, possibly on a scaffold. In this latter embodiment, ex vivo cell growth may be used to form a new tissue to be re-introduced into the subject, such as but not limited to a skin graft.

As used herein, an isolated cell is a cell that is physically removed from a subject. Preferably, an isolated cell is also substantially physically separated from other cell types with which it is normally present in vivo. Substantially physically separated means that the isolated cell represents a higher proportion of the cellular content in the isolated population than it represents in vivo. Accordingly, an isolated population generally is enriched for one or more cell types.

The invention also contemplates the implantation of a plurality of drug delivery systems at different sites in the body. As an example, if the subject is in need of tissue regeneration at various locations (e.g., in muscles), then it is possible to implant the drug delivery systems in muscular tissue in the limbs, back, neck, and the like, thereby stimulating muscular regeneration throughout the body.

The implant can be placed at any location in the body provided implantation (and in some instances, retrieval of the implant) is possible. For example, the implant can be introduced in or near the gastrointestinal epithelium, myocardium, regions of possible restenosis, heart, liver, lungs, intraperitoneal cavity, bone, bone marrow, cartilage, muscle, central nervous system, peripheral nervous system, mucosal tissues, mouth, throat, rectum, nasal tissues, lung and associated membranes, esophagus, trachea, spleen, kidney, urinary tract, bladder, pancreas, gall bladder, gonads and associated structures, and the like.

The implant may be introduced into a subject via surgical means or via non-surgical administration routes. These include but are not limited to oral administration, inhalation, intrathecal administration, intra-spinal administration, intra-peritoneal administration, intravascular administration, subcutaneous administration, intradermal administration, intramuscular administration, intrapericardial administration, intracranial administration, gastrointestinal administration, intra-liver administration, intra-lung administration, buccal administration, intra-kidney administration, intra-stomach administration, esophageal administration, topical administration and the like.

Some administration routes are more suitable to delivery of the implant, including subcutaneous, intramuscular, intradermal, intrapericardial, and the like. With some administration routes such as for example inhalation, preferably the implant consists of the drug delivery system in the absence of the external housing. For example, if the target tissue is the lungs or respiratory pathways, then the drug delivery system may be administered via inhalation thereby allowing the drug delivery system to contact and/or enter respiratory tissues such as the lungs. In these embodiments, it is less likely that the implant will be harvested from the subject.

Neural progenitor cells may be recruited or re-implanted into central nervous tissue such as but not limited to hippocampus, ventricle wall, neocortex, cerebellum, septal and striatal parenchyma, basal forebrain, hindbrain, mesencephalon, diencephalon, septum and spinal cord.

The implant or drug delivery system may include a physiologically or pharmaceutically acceptable carrier, excipient, or stabilizer. The term "pharmaceutically acceptable" means a non-toxic material that does not interfere with the effectiveness of the biological activity of the active ingredients. The term "pharmaceutically-acceptable carrier" means one or more compatible solid or liquid filler, dilutants or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

Drug delivery systems such as microparticles and nanoparticles may be administered to patients using a full range of routes of administration, albeit depending on the therapeutic embodiment. As an example, nanoparticles may be blended with direct compression or wet compression tableting excipients using standard formulation methods. The resulting granulated masses may then be compressed in molds or dies to form tablets and subsequently administered via the oral route of administration. Alternately nanoparticle granulates may be extruded, spheronized and administered orally as the contents of capsules and caplets. Tablets, capsules and caplets may be film coated to alter dissolution of the delivery system (enteric coating) or target delivery of the nanoparticle to different regions of the gastrointestinal tract. Additionally, nanoparticles may be orally administered as suspensions in aqueous fluids or sugar solutions (syrups) or hydroalcoholic solutions (elixirs) or oils. The nanoparticles may also be administered directly by the oral route without any further processing.

Nanoparticles may be co-mixed with gums and viscous fluids and applied topically for purposes of buccal, rectal or vaginal administration. Microspheres may also be co-mixed with gels and ointments for purposes of topical administration to epidermis for transdermal delivery.

Nanoparticles may also be suspended in non-viscous fluids and nebulized or atomized for administration of the dosage form to nasal membranes. Nanoparticles may also be delivered parenterally by either intravenous, subcutaneous, intramuscular, intrathecal, intravitreal or intradermal routes as sterile suspensions in isotonic fluids.

Finally, nanoparticles may be nebulized and delivered as dry powders in metered-dose inhalers for purposes of inhalation delivery. For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of for use in an inhaler or insufflator may be formulated containing the microparticle and optionally a suitable base such as lactose or starch. Those of skill in the art can readily determine the various parameters and conditions for producing aerosols without resort to undue experimentation. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Techniques for preparing aerosol delivery systems are well known to those of skill in the art. Generally, such systems should utilize components which will not significantly impair the biological properties of the agent in the nanoparticle or microparticle (see, for example, Sciarra and Cutie, "Aerosols," in *Remington's Pharmaceutical Sciences,* 18th edition, 1990, pp. 1694-1712; incorporated by reference).

Nanoparticles when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

The growth factors are administered via the implants and drug delivery systems in effective amounts. An effective amount of a particular agent will depend on factors such as the type of agent, the purpose for administration, the severity of disease if a disease is being treated etc. The effective amount for any particular application or agent being delivered may vary depending on such factors as the disease or condition being treated, the particular form of the agent being administered, the size of the subject, or the severity of the disease or condition. One of ordinary skill in the art can empirically determine the effective amount of a particular nanoparticle containing agent without necessitating undue experimentation.

The following Examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Summary

We demonstrate, for the first time, controlled release of bioactive molecules can recruit cells from the bone marrow into an ectopic porous mesh implant. Significant recruitment of lacz+ cells was observed to implants containing VEGF and GM-CSF loaded microspheres after 21 days. Remarkably, recruited lacz+ cells were "captured" entirely inside the implant.

Introduction:

The possibility of augmenting the body's own now recognized bone marrow reservoir of progenitor cells through the controlled release of specific growth factors is an intriguing therapeutic option that could significantly improve cardiovascular repair. Examples of growth factors that play a role in the recruitment of for example bone-marrow-derived endothelial progenitor cells (EPCs) include both vascular endothelial growth factor (VEGF) and granulocyte monocyte colony stimulating factor (GM-CSF). VEGF has been reported to increase the circulating concentration of EPCs (Kalka et al., Circ Res, 2000. 86(12): 1198-202), to be chemotactic for circulating endothelial progenitor cells (CEPs) (Rafii et al., Gene Therapy, 2002. 9:631-641), and to regulate and promote angiogenesis and vasculogenesis (Luttun et al., Trends Cardiovasc Med, 2002. 12(2):88-96). GM-CSF is reportedly released by bone marrow endothelial cells in response to VEGF in order to promote the growth of hematopoietic cells (Bautz et al., Exp Hematol, 2000. 28(6):700-6). Exogenous administration of GM-CSF was reported to mobilize EPCs and contribute to neovascularization (Takahashi et al., Nature Medicine, 1999. 5(4):434-438). According to the invention, it was hypothesized that the controlled release of growth factors like GM-CSF and VEGF from biodegradable microspheres could attract and stimulate progenitor cell populations from the bone marrow and ultimately aid patient populations that fail conventional medical and surgical therapy.

Experimental Methods:

Bone marrow transplant of lacz$^+$ cells:

Seven week old Rosa26 mice (B6;129S-Gtrosa26; The Jackson Laboratory, Bar Harbor, Me., USA) that transgenically express the bacterial lacz gene were used as donors for bone marrow transplantation. Seven week old B6;129S mice (The Jackson Laboratory) were used as recipients for the bone marrow transplant via tail vein injection. These mice were given a sublethal radiation dose of 950 rads (2 doses of 425 rads, each spaced 3-4 hours apart) from a 10,000 Ci 137-cesium irradiator (J.L. Shepard Co., Glendale, Calif.; model 68-A) the day before bone marrow transplant. Mice received sulfatrim: 200 mg sulfamethoxazole and 40 mg trimethoprim (Alpharma, Baltimore, Md.) one week prior to irradiation and for 4 weeks afterwards. Femurs, tibiae and humeri from Rosa26 mice were removed under sterile conditions and the cells harvested and collected into sterile DPBS (Mediatech, Inc., Herndon, Va.). Approximately $10\times10^6$ cells per mouse were transplanted into a total of 14 animals. Animals remained in sterile cage units post-transplantation until the time of surgery at 16 weeks of age.

The general strategy for the bone marrow transplantation arm of this study can be seen in FIG. 1.

Bone Marrow Engraftment:

To confirm transplantation of lacz$^+$ cells in a recipient mouse, an assay was designed to measure the number of lacz$^+$white blood cells in the mouse blood stream. White blood cells survive about 12-20 days, thus they should be reflective of bone marrow status. Eight weeks post-transplantation, approximately 30 µL of blood was collected from the tail veins of mice using heparinized hematocrit tubes (Drummon Scientific Co., Broomal, Pa.). After collection, blood was allowed to separate for 30-45 minutes and the 'upper phase" collected and spun down at 3000 rpm for 4 minutes. The supernatant was transferred to a 9:1 solution of 0.16 M $NH_4Cl$ and 0.17 M Tris (pH 7.65) (Sigma Chemical, St. Louis, Mo.), vortexed, and allowed to sit at room temperature for 4 minutes. After red blood cell lysis, the solution was centrifuged at 1500 rpm for 5 minutes and the supernatant decanted. The remaining white blood cells were suspended in 50 µL of staining buffer containing phosphate buffered saline (Sigma Chemical), 10 mM HEPES (Sigma Chemical) and 4% fetal bovine serum, (Gibco Co., Grand Island, N.Y.). Cells were warmed to 37° C. and then exposed to an equivalent volume of 2 mM fluorescein di-β-D-galactopyranoside at 37° C. After 5 minutes, the reaction was quenched with 1.8 mL of ice-cold staining medium containing 600 mM of chloroquine (Sigma Chemical) to inhibit endogenous galactosidases. The cells were then spun-down at 3000 rpm in flow cytometry tubes (Becton-Dickinson, San Jose, Calif.) and re-suspended in 220 µL of staining medium. The percentage of lacz$^+$ cells were assessed using a Becton Dickinson FACsCalibur Flow Cytometer by analyzing the number of cells containing the dye fluoroscein. Donor blood from Rosa26 mice and B6129S healthy mice served as positive and negative controls, respectively.

Microencapsulation:

A phase inversion nanoencapsulation technique was used for encapsulation of growth factors and cytokines as described previously (Hill et al. Cancer Res., 2002. 62(24): 7254-63).

(i) 0.1% Loaded VEGF and 0.1% BSA Control Microspheres

Microspheres were fabricated with 50:50 poly (DL-lactide-co-glycolide, MW=12,000) (Boehringer Ingleheim Inc. Germany) using a phase inversion technique. Briefly, a 50% solution of recombinant human vascular endothelial growth factor (rhVEGF$_{165}$), was combined with 10% bovine serum albumin and 10% Tween-20. This solution was added to a 0.001% polymer ethyl acetate solution and the two phase system vortexed and immediately shell-frozen, cooled in liquid $N_2$ followed by lyophilization for 48 hours. The dried polymer product was re-suspended in ethyl acetate (4% (w/v)) and the solution rapidly poured into petroleum ether (Fisher Scientific, Inc.) for formation of microspheres that were filtered and lyophilized for 48 hours for complete removal of solvent. Control spheres were made following exactly the same procedure with the exception of the replacement of VEGF with bovine serum albumin (Sigma Chemical).

(ii) 0.2% Loaded GM-CSF and BSA Control Microspheres

Poly-L-lactide (PLA, 8k) (Lactel, RL104.BI, batch #33007) and PLA 24K (Lactel, 505-25-A) was used for the encapsulation of mGM-CSF (Biosource International, Camarillo, Calif.). A similar encapsulation procedure was employed as above with the exception that methylene chloride was used in place of ethyl acetate. Control spheres were made following exactly the same procedure with the exception of the replacement of GM-CSF with bovine serum albumin (Sigma Chemical).

Release Kinetics of Loaded Microspheres:

Microsphere encapsulation of VEGF was designed to release continuously above the known physiologically active range (ED$_{50}$ 2-6 ng/ml) for 3-4 weeks. Microspheres were divided into 4 groups per time point and re-suspended in EBM-2 media (Clonetics) at an estimated concentration of 0.2 mg rhVEGF$_{165}$/mL of solution. Sterile 2 mL tubes were incubated at 37° C. and supernatant removed at appropriate time points. The reserved supernatant was stored at −20° C. until analysis. rhVEGF$_{165}$ release was determined using an ELISA kit specific for rhVEGF$_{165}$ (Chemicon, CA). Concentrations of rhVEGF$_{165}$ were determined by standard curve.

The release for GM-CSF was conducted as above with the ELISA kit also from Chemicon.

Implant Fabrication:

0.8 cm×0.8 cm squares of nylon mesh (SpecraMesh, CA) with a pore size of 20 microns were heat sealed on three sides and sterilized (Amsco Gravity 2051 autoclave). Appropriate microspheres were added to each "bag" and the fourth side heat-sealed prior to surgery. Groups included sham (empty nylon mesh bag only, n=2), mesh containing 6 mg of 0.1% and 2 mg of 0.2% BSA loaded microspheres (n=3), mesh containing 6 mg of 0.1% VEGF loaded microspheres (n=3), mesh containing 2 mg of 0.2% GM-CSF loaded microspheres (n=3), and a mesh containing both VEGF (6 mg) and GM-CSF (2 mg) microspheres (n=3).

Figure 2A:
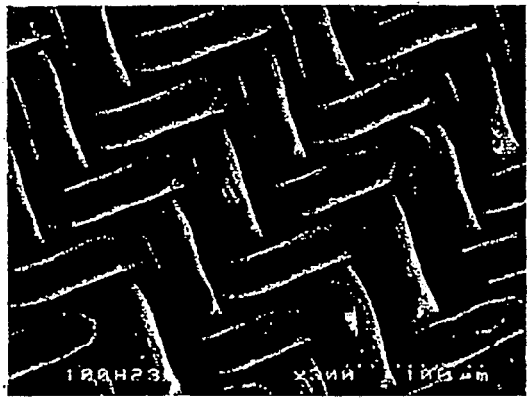
FIG. 2A shows a scanning electron micrograph of a nylon mesh pre-implantation. Pores were found to be between 15-20 microns.
Figure 2B:
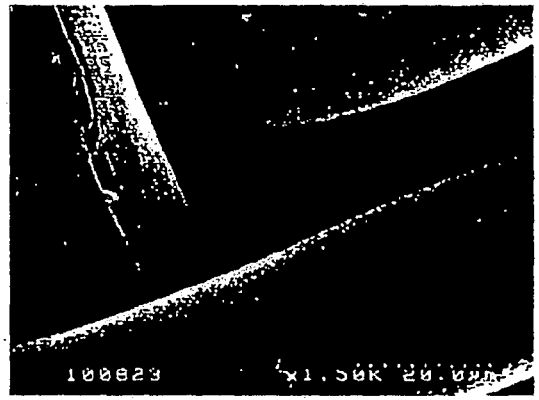
FIG. 2B provides a higher magnification micrograph corresponding to FIG. 2A.

A scanning electron micrograph of a nylon mesh pre-implantation is shown in FIG. 2. The pore size was determined to be about 15-20 microns.

Animal Surgery:

Nylon pouches containing microspheres were implanted subcutaneously into the dorsal aspect of 16 week old B6129S mice (9 weeks post-transplantation). The mouse was anesthetized in an asphyxiation chamber with administration of inhalational isofluorane®. Anesthesia was maintained throughout the procedure by the administration of inhalational isofluorane® via a nose cone. A 1 cm incision was made just lateral to the spine in the right upper dorsal quadrant. After implant placement, the wound was closed using running sutures (Vicryl 6-0). After 21 days, animals were sacrificed using an overdose of metofane. Implants and adjacent skin were immediately removed, placed in OCT embedding medium (Sakura Finetek Inc. Torrance, Calif.) and quick-frozen on dry ice. A Leica CM1510 cryostat (Leica Microsystems, Germany) was used to take 14 micron frozen sections of implant cross-sections. Sections were stored at −20° C. until staining.

Identification of Recruited lacz$^+$ cells:

Cryosections of the implant and adjacent skin were washed in PBS (pH 7.5) (Sigma Chemical) to remove OCT embedding medium and fixed for four minutes in 2% paraformaldehyde (Electron Microscopy Sciences, Fort Washington, Pa.). Slides were washed 3× in PBS (pH=7.5), 2× in 2 mM MgCl$_2$ PBS, pH 7.5, and 1× in staining solution (see below) without X-gal. Slides were then incubated at 37 C for 8-16 hours with the X-gal staining solution prepared in PBS. The staining solution contained 5 mM K$_3$Fe(CN)$_6$, 5 mM K$_4$Fe(CN)$_6$.3H$_2$O, 2 mM MgCl$_2$, pH 7.5 and 1 mg/ml X-gal (Sigma Chemical). Sections were then washed in PBS, dehydrated, and mounted in xylene:permount (50:50) (Fisher Scientific, Inc.) and viewed using a light microscope (Olympus, IX70) and pictures taken using a digital camera at magnifications from 1.25×-20×.

Results:

B6129S engraftment post-transplantation was measured using flow cytometry to assess the number of lacz$^+$ white blood cells in samples. Mice implanted with blank mesh were approximately 79% +/−14% engrafted, mice implanted with BSA spheres and mesh were approximately 68% +/−7% engrafted, mice implanted with GM-CSF spheres and mesh were approximately 59% +/−16% engrafted, mice implanted with VEGF spheres and mesh were approximately 68% +/−13% engrafted, and mice implanted with VEGF/GM-CSF spheres and mesh were approximately 81% +/−10% engrafted. An ANOVA statistical analysis revealed no differences between groups.

ELISA analysis of VEGF and GM-CSF loaded microspheres demonstrated continuous release of each factor over the study time frame. Each formulation had a burst of factor released on day 1 (approximately 0.91 mg/mouse for VEGF and 1.525 mg/mouse for GM-CSF) followed by a reasonably constant release (0.5-1 ng GM-CSF/mouse/day and 0.3-1 ng VEGF/mouse/day).

Figure 3A:
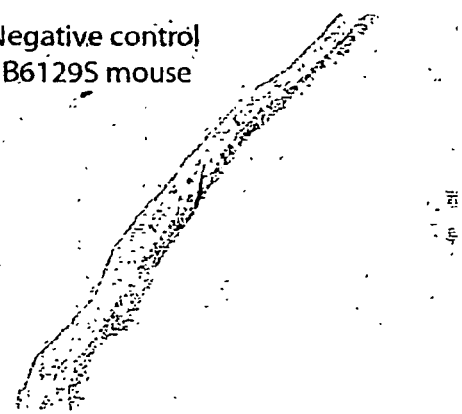
FIG. 3A shows the light microscopy brightfield images of skin cross sections taken from B6;129S mouse. These showed no positive beta-galactosidase staining. (Magnification 1.25×.)
Figure 3B:
FIG. 3B shows the light microscopy brightfield images of skin cross sections taken from Rosa26 mouse used for bone marrow transplantation. These showed positive staining throughout the tissue section. (Magnification 1.25×.)

To confirm positive beta-galactosidase staining, sections of mouse tissue from control mice (B6;129S) and Rosa26 were taken and cryo-sectioned as described above. No blue staining was seen in the negative control mouse tissue and skin from the Rosa 26 mouse contained positive blue staining denoting lacz$^+$ cells in the dermis, blood vessels, plantar muscularis and in the hypodermis. (FIGS. 3A and 3B.)

Figure 4A:
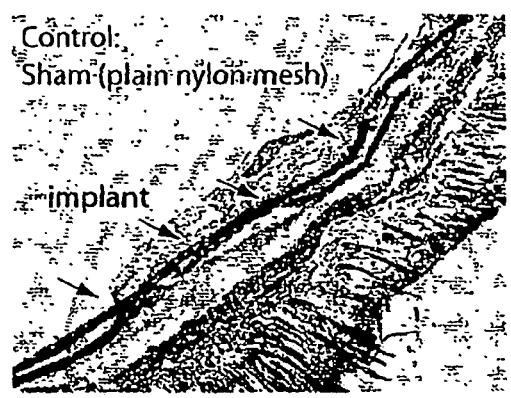
FIG. 4A is a cross section of a control (plain nylon mesh) showing that a few lacz$^+$ cells can be found along the nylon mesh but no cells were found inside the implant. (Magnification 1.25×.)
Figure 4B:
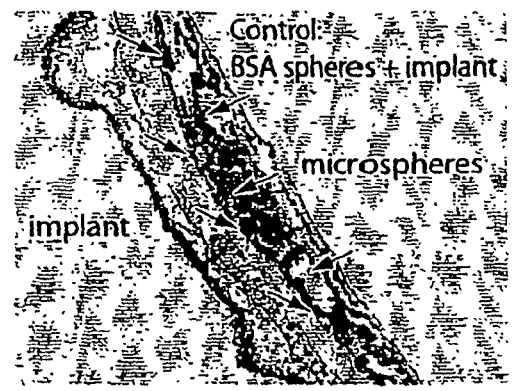
FIG. 4B is a cross section of a control (BSA spheres and implant) showing that no lacz$^+$ cells can be found inside the implant or in the skin adjacent to the implant. (Magnification 1.25×.)
Figure 4C:
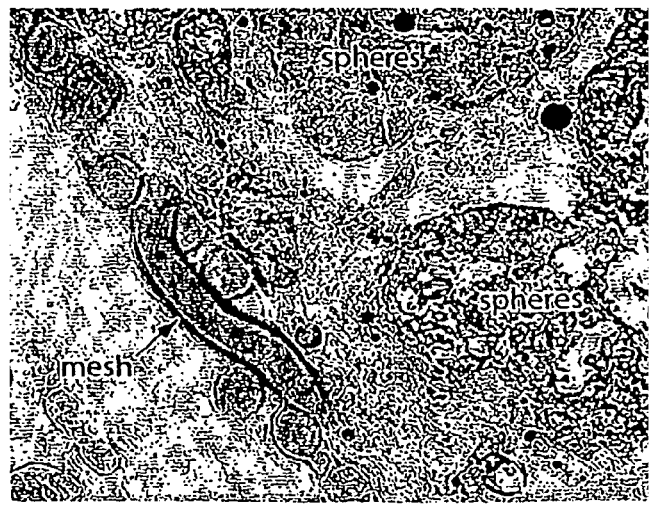
FIG. 4C is a higher magnified view of a cross section of a control (BSA spheres and implant) showing that no lacz$^+$ cells are present inside the implant or in the skin adjacent to the implant. (Magnification 20×.)

In order to rule out cell recruitment due to the nylon mesh itself or the degradation products of PLGA or PLA microspheres, two more controls were included in the study: a sham implant and a nylon mesh implant loaded with BSA control microspheres. Occasional blue staining was found along the cross-section of the sham implant, but few or no blue cells were found inside the implant. No of lacz$^+$ cells were found in skin adjacent to the BSA control implant or within the nylon mesh itself. (FIGS. 4A, 4B and 4C.)

Figure 5A:
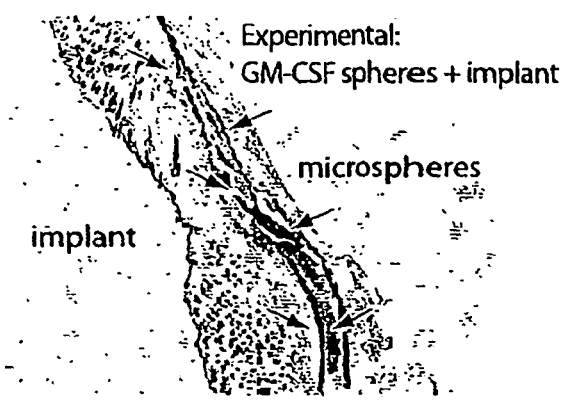
FIG. 5A shows the staining pattern of an implant containing PLA microspheres loaded with GM-CSF. Some cellular infiltration was found within the implant but no lacz$^+$ cells could be seen in adjacent tissue or within the implant. (Magnification 1.25×.)
Figure 5B:
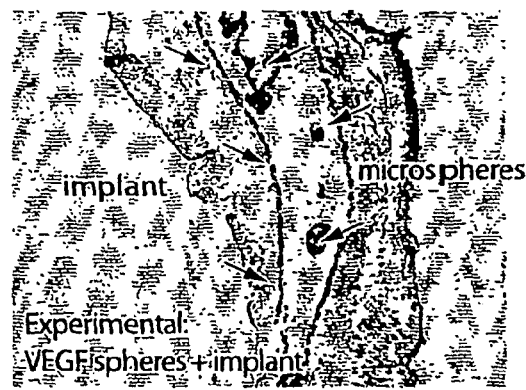
FIG. 5B shows the staining pattern of an implant containing PLGA microspheres loaded with VEGF. Significant cellular infiltration of the mesh implant is seen, but relatively few lacz$^+$ cells are present. (Magnification 1.25×.)
Figure 5C:
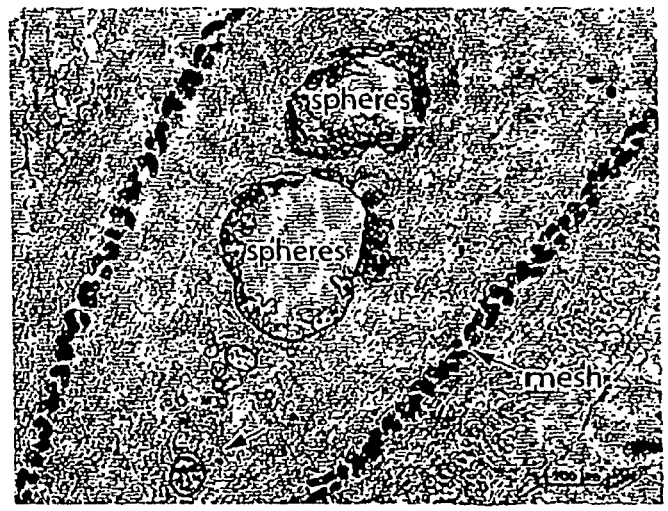
FIG. 5C shows the staining pattern of an implant containing PLGA microspheres loaded with VEGF. Significant cellular infiltration of the mesh implant can be found. At higher magnification, some lacz$^+$ cells are present (arrow). (Magnification 4×.)

To test the ability of GM-CSF and VEGF to individually recruit cells from the bone marrow to an ectopic site in an adult mouse, each factor was encapsulated into PLA or PLGA microspheres respectively and placed inside a nylon mesh bag which was implanted into murine subjects for 3 weeks. Few lacz$^+$ cells positive cells could be found in sections of implants containing either growth factor alone. (FIGS. 5A, 5B and 5C.)

Figure 6A:
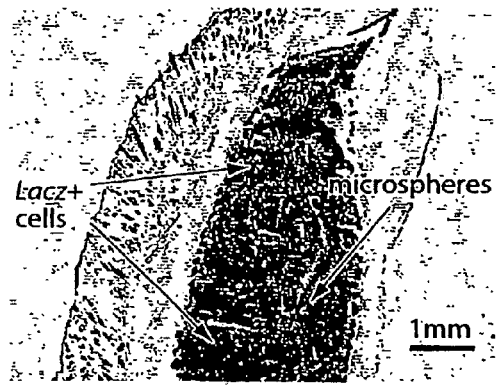
FIG. 6A shows the cross-sectional staining pattern of an implant containing a VEGF/GM-CSF implant. Significant cellular infiltration of the implant space was seen with the vast majority of cells lacz$^+$. Some lacz$^+$ cells were found outside the margin of the implant. (Magnification 1.25×.)
Figure 6B:
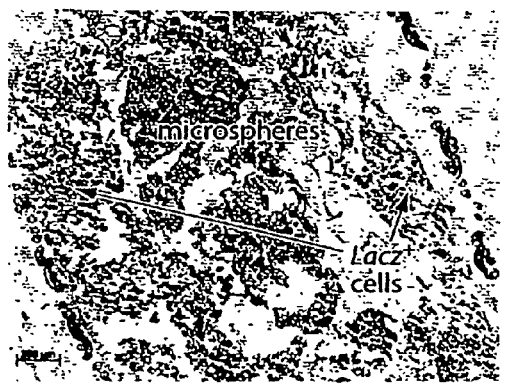
FIG. 6B shows another cross-section of a VEGF/GM-CSF nylon mesh subcutaneous implant from a different animal. Significant cellular infiltration of the implant space was seen with the vast majority of cells lacz$^+$. No lacz$^+$ were found outside the margin of the implant. (Magnification 4×.)

To test possible synergy between VEGF and GM-CSF, an implant containing both types of microspheres was tested as well. Cellular infiltration into the nylon mesh was significant and the majority of cells were lacz $^+$. Many lacz$^+$ cells were found in the tissue adjacent to the implant. (FIGS. 6A and 6B.)

Table 3 summarizes X-gal staining results of sections taken from animals M1-M14. In general, there were only a few lacz$^+$ cells within all implants with the exception of implants containing both VEGF and GM-CSF loaded microspheres. Blood vessels found in tissue adjacent to these implants also contained lacz$^+$ cells.

TABLE 3

| Animal/Group | Lacz$^+$ cells within implant | Lacz$^+$ cells in tissue superior to implant |
|---|---|---|
| Nylon mesh only | | |
| M9 | 1-2 cells | None |
| M11 | None | Some lining nylon mesh (not CD133$^+$) |
| Mesh + BSA spheres | | |
| M4 | None | None |
| M5 | 1 cell | None |
| M10 | A few cells near microspheres (not CD133$^+$) | None |
| Mesh + VEGF spheres | | |
| M1 | None | None |
| M7 | Yes. Several cells found near spheres and dispersed in implant matrix (CD133$^+$) | Yes. lacz$^+$ cells within wall of vascular structures |
| M12 | None | None |
| Mesh + GM-CSF spheres | | |
| M2 | None | None |
| M6 | None | None |
| M13 | 1-2 cells | Some cells. A few lacz$^+$ cells within wall of vascular structures |
| Mesh + VEGF/ GM-CSF spheres | | |
| M3 | Yes. Lacz$^+$ cells dispersed throughout implant | Yes. Lacz$^+$ cells within walls of vascular structures |

TABLE 3-continued

| Animal/Group | Lacz+ cells within implant | Lacz+ cells in tissue superior to implant |
|---|---|---|
| M8 | Yes. Lacz+ cells dispersed throughout implant | Yes. Lacz+ cells within walls of vascular structures and dispersed in tissue |
| M14 | Yes. Lacz+ cells dispersed throughout implant | Yes. Lacz+ cells within walls of vascular structures |

Conclusions:

The work described above provides evidence that the controlled release of growth factors can mobilize cells from the bone marrow into the bloodstream and these cells can be recruited to a specific site remote from the vascular system in an adult animal. It is important to note that the mice at the time of surgery were 16 weeks old, an age considered advanced in mouse years.

Furthermore, this study demonstrates that through specific study design, these cells can be entirely "captured" within a porous mesh bag and thereby extracted from the host animal. These cells could then be cultured ex vivo and transplanted back into the host or used therapeutically in another host.

Example 2

Summary

Implants containing unencapsulated VEGF and GM-CSF do not recruit lacz+ cells from the bone marrow at 21 days.

Experimental Methods:

B6129S female mice were prepared with the lacz+ bone marrow transplant as described above. 8-10 weeks post-transplantation and confirmation of engraftment, implants containing VEGF and GM-CSF solutions were implanted in the dorsal subcutaneous space as described above. Using ELISA data, the total amount of VEGF and GM-CSF released from microspheres over the course of 21 days was calculated. Solutions containing 0.925 mg of VEGF and 1.54 mg of GM-CSF were placed within the nylon mesh and implanted. After 21 days, implants were excised and processed for tissue histology as described above.

Figure 7A:
FIG. 7A shows an X-gal stained cross-section of a mesh implant containing unencapsulated VEGF/GM-CSF spheres after 21 days of implantation. No lacz$^+$ cells can be found within implant or exterior to the implant perimeter. The nylon mesh implant perimeter is clearly seen. A survey of all of the cells that invaded the mesh implant revealed no bone marrow recruited cells. (Magnification 4×.)
Figure 7B:
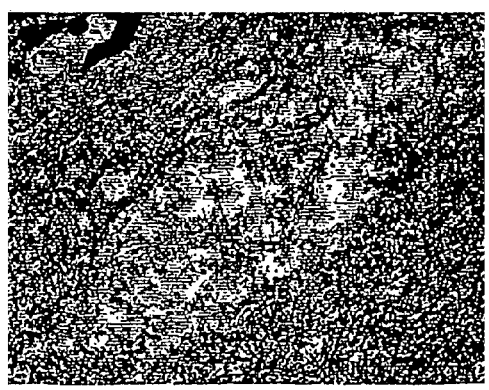
FIG. 7B is a higher magnified view of interior of implant of FIG. 7A. (Magnification 10×.)

Results:

No lacz+ cell recruitment was observed to mesh implants containing a bolus dose of unencapsulated VEGF and GM-CSF (FIGS. 7A and 7B). No lacz+ cells can be found within the implant or exterior to the implant perimeter. It should be noted, that the entire total dose of either VEGF or GM-CSF respectively was added to the mesh although the post-encapsulation bioactivity of each protein was estimated to be approximately 50%.

Conclusions:

Controlled release of each factor is an important and integral component of the implant and process of recruitment and capture of progenitor cells.

Example 3

Summary

CD133+ stem cells were identified in implant sections containing VEGF and GM-CSF as demonstrated using immunohistochemistry and confocal scanning laser microscopy.

Experimental Methods:

Sections of mouse bone marrow were stained for CD133 concurrently as a positive control. Secondary antibody only and no secondary antibody controls were also included. All CD133 staining was viewed in the far red region, thus minimizing the possibility that positive staining is a result of nonspecific autofluoresence. Briefly, frozen sections were brought to room temperature and OCT embedding medium dissolved in PBS. Sections were permeabilized with 0.1% Triton X-100 (Sigma Chemical) in a solution containing 4% bovine serum albumin (Sigma Chemical) and 10% goat serum (Jackson ImmunoResearch Laboratories, Inc., West Grove, Pa.) for 1 hour. A monoclonal anti-CD133 antibody (R & D Systems, Minneapolis, Minn.) in blocking solution was applied to each section and allowed to incubate overnight at 4° C. The sections were rinsed, blocked with 4% BSA/10% goat serum for 1 hour and the secondary antibody applied (Alexa 647 nm, Molecular Probes, Oregon). All sections were counterstained using Dapi to visualize nuclei. (Slow Fade mounting media, Molecular Probes)

Results:

Table 4 summarizes the CD133 staining results after a 3 week subcutaneous implantation of VEGF and GM-CSF loaded microspheres. No CD133+ cells were found in any of the negative control groups: sham (n=2) and BSA microspheres (n=3). Some CD133+ cells were found within implants containing either VEGF or GM-CSF, but their numbers were lower than that observed in the combination implant. VEGF alone appeared to recruit more CD133+ cells than GM-CSF alone.

TABLE 4

| Group | CD133 Staining Summary |
|---|---|
| Sham Nylon Implant | |
| M9 | None |
| M11 | None |
| BSA microspheres | |
| M4 | None |
| M5 | None |
| M10 | None |
| VEGF microspheres | |
| M1 | Many CD133+ cells within mesh (not > than M14) |
| M7 | A few CD133+ cells within mesh |
| M12 | Several CD133+ cells - in between M1 and M12 |
| GM-CSF microspheres | |
| M2 | A few more CD133+ cells than M6 but very few overall |
| M6 | Very few CD133+ cell |
| M13 | None |
| VEGF/GM-CSF microspheres | |
| M3 | Lots of cell death - evidence pointing towards CD133+ cells (diffuse red staining) |
| M8 | A few CD133+ cells but lots of cell death and overall difficult to assess |
| M14 | Many CD133+ cells - more compared to any other group - majority of cells located within mesh were positive for CD133 |

(i) Nylon mesh implants without microspheres: Shams M9 & M11 (n = 2)

Figure 8:
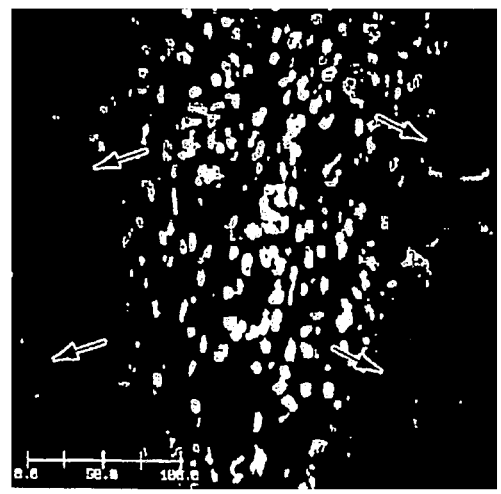
FIG. 8 is a representative confocal scanning microscope image of cells located within mesh implants. No CD133$^+$ cells were found within the implant or within 400 μm of the implant perimeter. The implant boundary is denoted by the white arrows. Cell nuclei are counterstained in dapi (blue). (Original magnification 40×.)

FIG. 8 shows that no CD133+ cells were found within the sham implant or within 400 μm of the sham implant perimeter. The sham implant boundary is denoted by the white arrows. Cell nuclei are counterstained in dapi (blue).

Figure 9A:
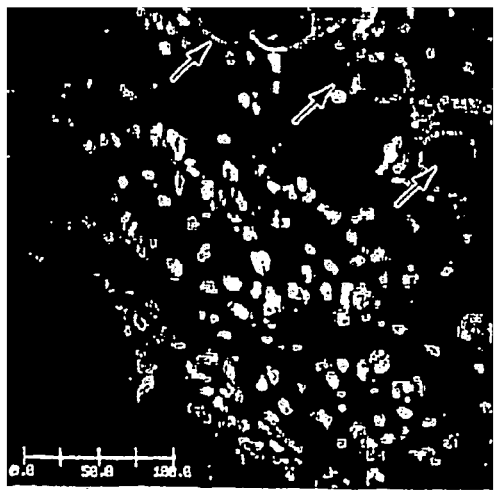
FIG. 9A is a representative confocal image of a cross-section taken from the second sham animal (M11). No CD133+ cells were found within the implant. White arrows denote nylon mesh implant. (Original magnification 40×.)
Figure 9B:
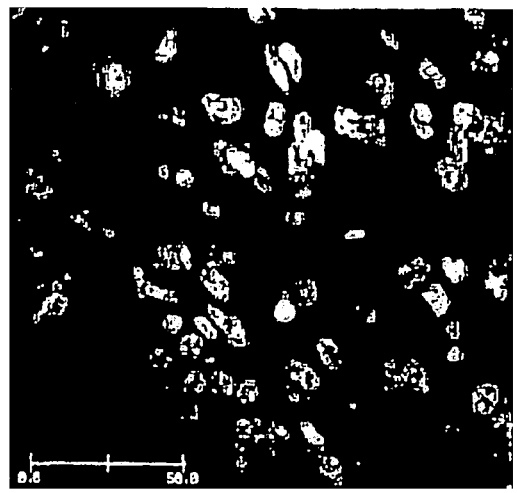
FIG. 9B is a representative confocal image of a cross-section taken from the second sham animal (M11) dapi-stained to identify nuclei (blue). No CD133+ cells are present. (Original magnification 80×.)

FIGS. 9A and 9B similarly show that no CD133+ cells were found within the sham implant. White arrows denote nylon mesh implant.

(ii) Nylon Mesh Implants with 2% BSA Loaded Microspheres: M4, M5 M10 (n=3)

Figure 10A:
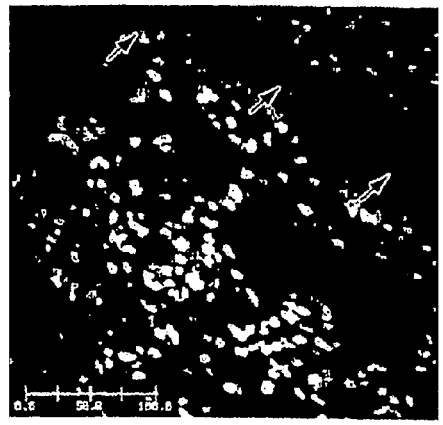
FIG. 10A is a representative confocal scanning image of a cross-section taken from an animal implanted with 2% BSA spheres (M4). No CD133+ cells were found within or external to the implant. White arrows denote nylon mesh. (Original magnification 40×.)
Figure 10B:
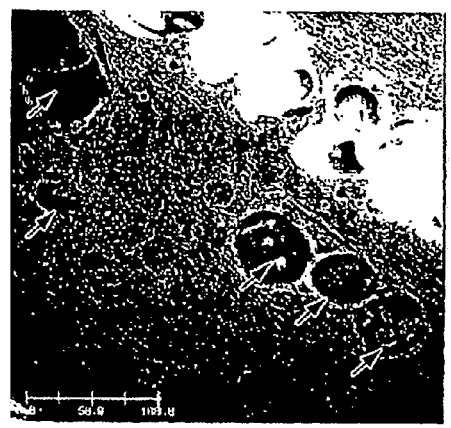
FIG. 10B is a DIC brightfield image of same implant site as FIG. 8A. Microspheres are clearly identified with white arrows. (Original magnification 40×.)

FIGS. 10A and 10B show that no CD133+ cells were found within or external to the BSA implant. White arrows denote nylon mesh (in A) and microspheres (in B).

Figure 11A:
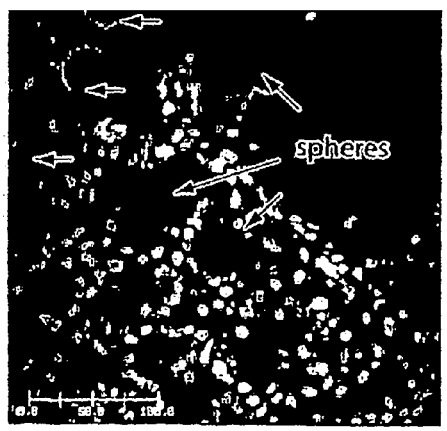
FIG. 11A is a representative confocal scanning image of a cross-section taken from an animal implanted with 2% BSA spheres (M5). No CD133+ cells were found within or external to the implant. Short white arrows denote nylon mesh. (Original magnification 40×.)
Figure 11B:
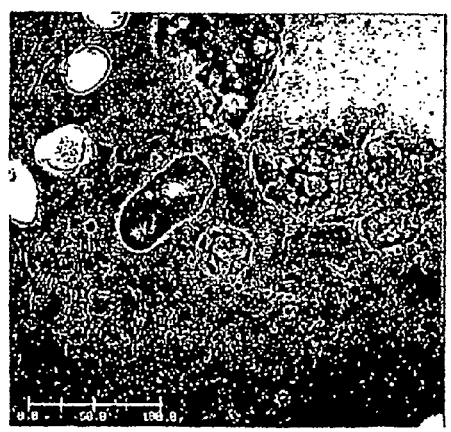
FIG. 11B is a DIC brightfield image of same implant site as FIG. 9A. Microspheres can be seen clearly. (Original magnification 40×.)

FIGS. 11A and 11B show that no CD133+ cells were found within or external to the BSA implant. Short white arrows denote nylon mesh (in A).

FIGS. 12A and 12B show that no CD133+ cells were found within or external to the BSA implant. Nuclei are stained blue (dapi).

(iii) Nylon Mesh Implants with GM-CSF Loaded Microspheres: M2, M6, M13 (n=3)

FIGS. 13A and 13B show that some CD133+ cells (punctate red staining) were found dispersed throughout the GM-CSF implant. Nuclei are stained blue (dapi).

Figure 14A:
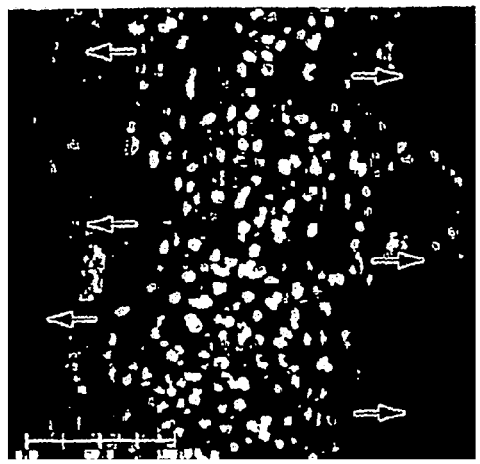
FIG. 14A is a representative confocal image of a cross-section taken from an animal implanted with a nylon mesh loaded with GM-CSF microspheres (M6). Very few CD133+ cells (red staining) were found. Short white arrows denote nylon mesh. (Original magnification 40×.)
Figure 14B:
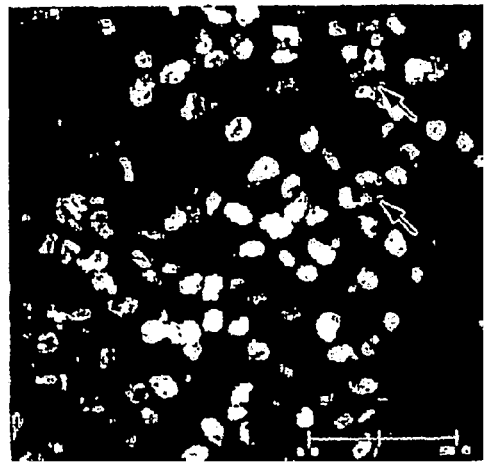
FIG. 14B is a close-up confocal image of a cross-section taken from an animal implanted with a nylon mesh loaded with GM-CSF microspheres (M6) showing dapi-stained nuclei (blue) and occasional CD133+ cells (red) denoted by white arrows. (Original magnification 80×.)

FIGS. 14A and 14B show that very few CD133+ cells (red staining) were found in GM-CSF implants. Short white arrows denote nylon mesh (in A) and CD133+ cells (in B). Nuclei are stained blue (dapi).

Figure 15A:
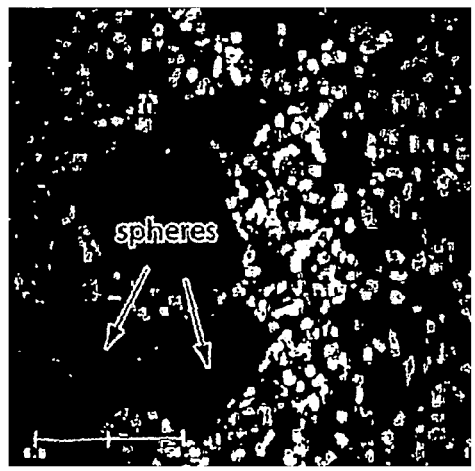
FIG. 15A is a representative confocal image of a cross-section taken from an animal implanted with a nylon mesh loaded with GM-CSF microspheres (M13). No CD133+ cells were found. (Original magnification 40×.)
Figure 15B:
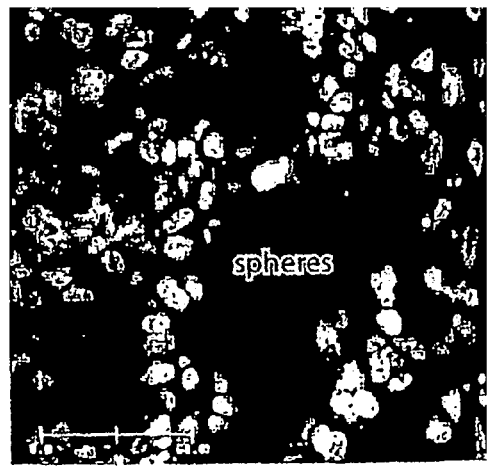
FIG. 15B is a close-up confocal image of a cross-section taken from an animal implanted with a nylon mesh loaded with GM-CSF microspheres (M13) showing dapi-stained nuclei (blue). (Original magnification 80×.)

FIGS. 15A and 15B show that no CD133+ cells were found GM-CSF implants. Nuclei are stained blue (in B).

(iv) Implants Containing VEGF Loaded Microspheres: M1, M7, M12 (n=3)

Figure 16A:
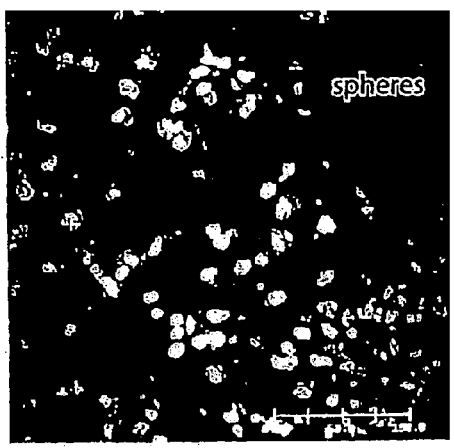
FIG. 16A is a representative confocal scanning laser image of a cross-section taken from an animal implanted with a nylon mesh loaded with VEGF microspheres (M1). Many CD133+ cells (red staining) were found in close proximity to groups of PLGA microspheres. (Original magnification 40×.)
Figure 16B:
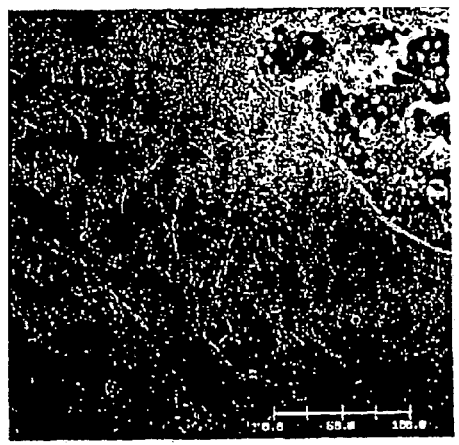
FIG. 16B is a DIC brightfield image of the same implant site as in FIG. 14A. PLGA microspheres can be seen clearly (Original magnification 40×.)
Figure 16C:
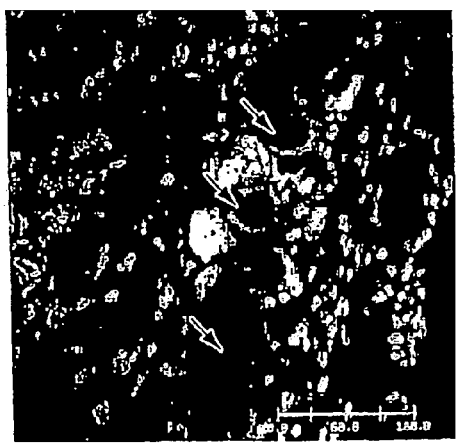
FIG. 16C is a close-up confocal scanning laser image of a cross-section taken from an animal implanted with a nylon mesh loaded with VEGF microspheres (M1) showing dapi-stained nuclei (blue). (Original magnification 80×.)

FIGS. 16A, 16B and 16C show that CD133+ cells (red staining) were sometimes found in close proximity to groups of PLGA VEGF microspheres. PLGA microspheres can be seen clearly in B. Nuclei are stained blue (dapi) in C.

Figure 17A:
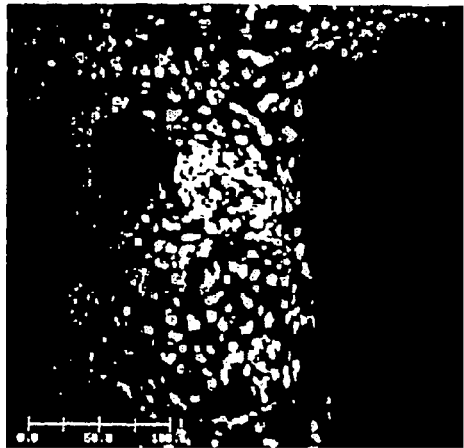
FIG. 17A is a representative confocal scanning laser image of a cross-section taken from an animal implanted with a nylon mesh loaded with VEGF microspheres (M7). Few CD133+ cells (red staining) were found in close proximity to groups of PLGA microspheres. (Original magnification 40×.)
Figure 17B:
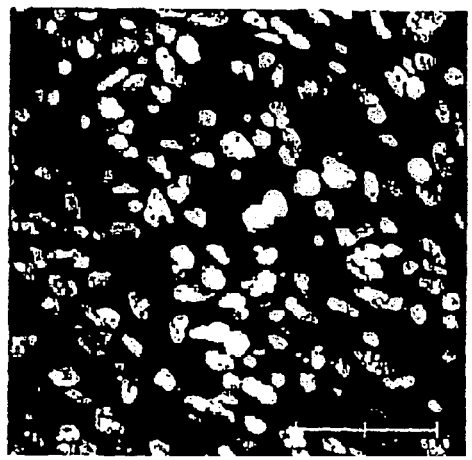
FIG. 17B is a close-up confocal scanning laser image of a cross-section taken from an animal implanted with a nylon mesh loaded with VEGF microspheres (M7) showing dapi-stained nuclei (blue). (Original magnification 80×.)

FIGS. 17A and 17B show that some CD133+ cells (red staining) were found in close proximity to groups of PLGA microspheres. Nuclei are stained blue (dapi) in B.

Figure 18A:
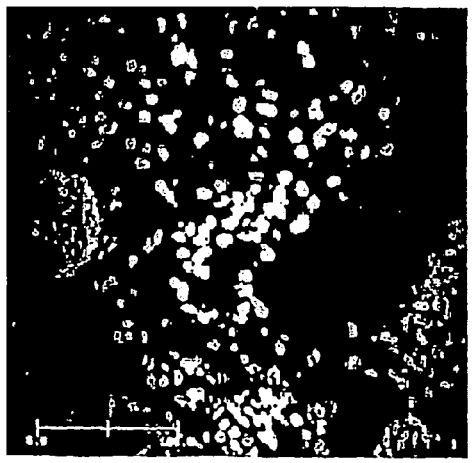
FIG. 18A is a representative confocal scanning laser image of a cross-section taken from an animal implanted with a nylon mesh loaded with VEGF microspheres (M12). Some CD133+ cells (red staining) were found in close proximity to groups of PLGA microspheres. (Original magnification 40×.)
Figure 18B:
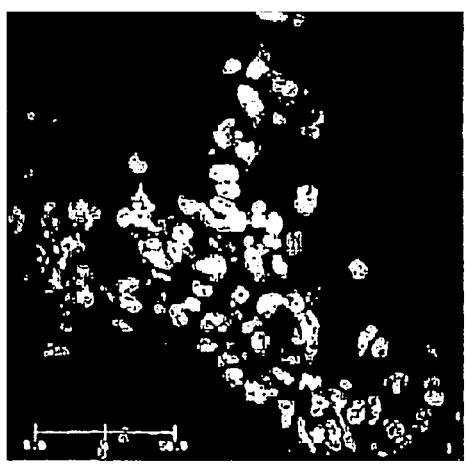
FIG. 18B is a close-up confocal scanning laser image of a cross-section taken from an animal implanted with a nylon mesh loaded with VEGF microspheres (M12) showing dapi-stained nuclei (blue). (Original magnification 80×.)

FIGS. 18A and 18B shows that some CD133+ cells (red staining) were found in close proximity to groups of PLGA microspheres. Nuclei are stained blue (dapi) in B. There appeared to be some random variability in the number of CD133+ cells in close proximity to microspheres loaded with VEGF alone. Mouse M1 had more CD133 cells than mice M7 and M12 and these cells were located most frequently near microspheres. VEGF alone is able to recruit some CD133 cells but it is not as robust as the combination of VEGF/GM-CSF where >95% of the cells within the mesh were recruited from the bone marrow (based on lacz staining). About 1-3% of the cells recruited to the VEGF implant stained positive for lacz.

(v) Implants Containing VEGF/GM-CSF Loaded Microspheres: M3, M8, M14 (n=3)

Figure 19A:
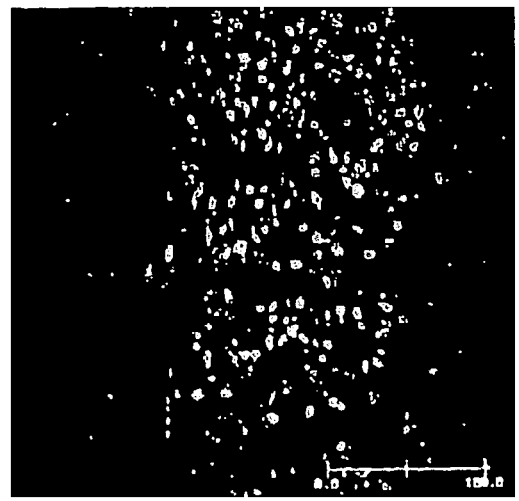
FIG. 19A is a representative confocal scanning laser image of a cross-section taken from an animal implanted with a nylon mesh loaded with VEGF and GM-CSF microspheres (M14). Many CD133+ cells (red staining) were found in close proximity to groups of PLGA microspheres. (Original magnification 40×.)
Figure 19B:
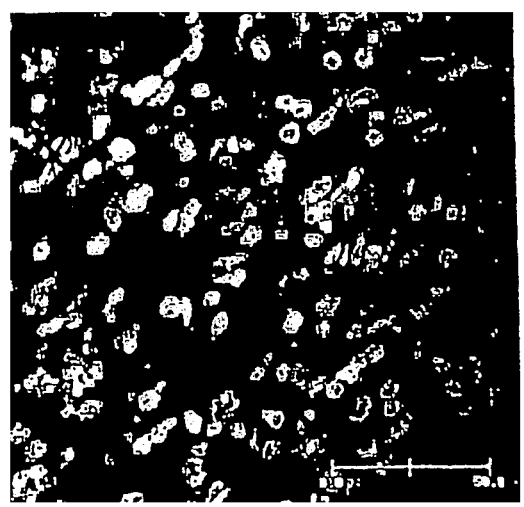
FIG. 19B is a close-up confocal scanning laser image of a cross-section taken from an animal implanted with a nylon mesh loaded with VEGF and GM-CSF microspheres (M14) showing dapi-stained nuclei (blue) cells positive for CD133. (Original magnification 80×.)

FIGS. 19A and 19B show that many CD133+ cells (red staining) were found in close proximity to groups of PLGA VEGF/GM-CSF microspheres. Nuclei are stained blue (dapi) in B. Similar staining patterns are seen after 1 or 2 weeks of implantation.

Conclusions:

Endothelial progenitor cells were identified in and near the implants containing VEGF alone and VEGF/GM-CSF. These findings support the ability to recruit progenitor cells from the bone marrow to other locations in the body. The continuous release of both VEGF alone or GM-CSF and VEGF together results in a permissive microenvironment capable of recruiting and nurturing primitive progenitor cells.

Example 4

Summary

Nylon mesh implants containing VEGF and GM-CSF microspheres recruit lacz+ cells from the bone marrow as early as 7 and 14 days after implantation.

Experimental Methods:

B6129S female mice were prepared according to the lacz+ bone marrow transplant protocol described above. Eight to ten weeks post-transplantation and confirmation of engraftment, implants containing VEGF and GM-CSF microspheres containing implants and control implants were placed in the dorsal subcutaneous space of murine subjects as described above.

Groups at 7 days included: nylon mesh (n=2), mesh+BSA spheres (n=2), mesh+unencapsulated VEGF and GM-CSF (n=2), mesh+GM-CSF loaded micro spheres (n=3), mesh+VEGF loaded microspheres (n=3), and mesh+VEGF/GM-CSF loaded microspheres (n=3).

Groups at 14 days included: nylon mesh (n=2), mesh+BSA spheres (n=2), mesh+GM-CSF loaded microspheres (n=4), mesh+VEGF loaded microspheres (n=4), and mesh+VEGF/GM-CSF loaded microspheres (n=5).

After 7 or 14 days, implants were excised and processed for tissue histology as described above.

Results:

Analysis of VEGF/GM-CSF loaded microsphere implants at 7 and 14 days shows strong lacz+ cell recruitment to the area inside the mesh. The majority of cells stain blue using the X-gal staining technique.

Figure 20A:
FIG. 20A shows the frozen cross-section of implant and attendant skin embedded in OCT cryostat medium after 1 week in vivo. This implant contained both VEGF and GM-CSF loaded microspheres. The outline of the implant/nylon mesh is clearly demarcated within the subcutaneous space. Microspheres are located at both ends and look like white regions within the implant.

FIG. 20A shows a frozen cross-section of an implant and attendant skin from the subcutaneous space after one week in vivo. This implant contained both VEGF and GM-CSF loaded microspheres. There is a significant number of cells (yellowish region bounded by implant) recruited to an implant after 1 week. Microspheres can be viewed in left- and right-hand corners of the implant. The majority of these cells stain lacz+ demonstrating the recruitment from the bone marrow. Recruited cells are found most densely in the implant center and resemble a yellow, marrow-like tissue.

Figure 20B:
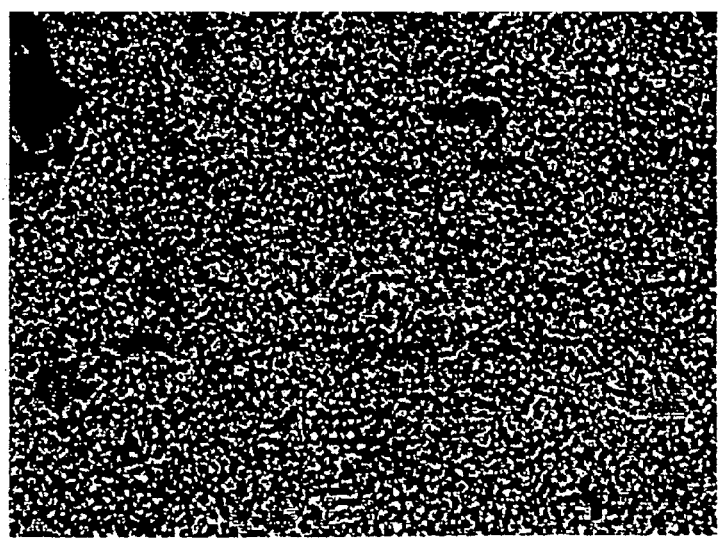
FIG. 20B shows X-gal staining of the VEGF/GM-CSF implant after 7 days in vivo. (Original magnification 20×.)
Figure 20C:
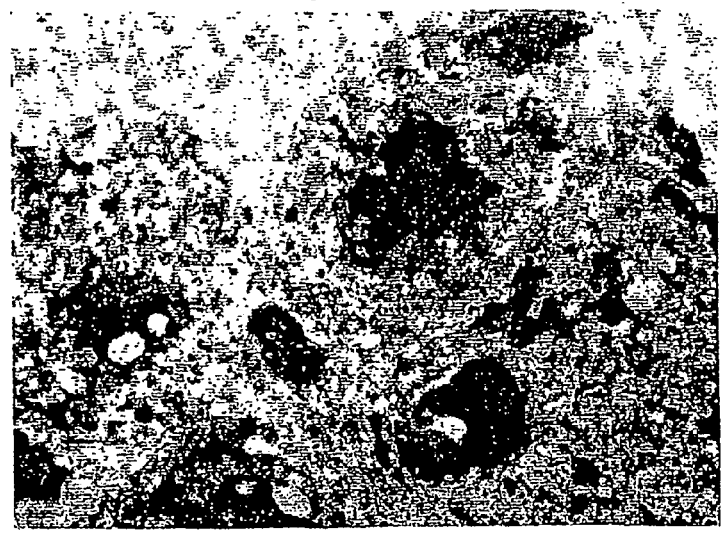
FIG. 20C is a transmission electron micrograph (TEM) showing cells isolated from a 1 week old VEGF/GM-CSF microsphere loaded implant. Cells were 2-5 microns in diameter and displayed a rounded morphology. A significant portion of the cell was comprised of the nucleus, suggesting a progenitor cell phenotype.

FIG. 20B shows X-gal staining of the VEGF/GM-CSF implant after 7 days in vivo. The majority of cells within the implant stained lacz+. Cell morphology was very consistent with spherical cells ranging between 2-5 microns. Transmission electron micrograph (TEM) analysis of cells reveals that the nucleus predominates the entirety of the cell suggesting an early stem/progenitor cell phenotype (FIG. 20C).

Conclusions:

Lacz+ cells are recruited to the area mesh as early as 1 week. Earlier time periods of recruitment are possible.

Example 5

Summary

Progenitor cells may be extracted from an implant and cultured in vitro.

Experimental Methods:

After 1 week, a B6129S transgenic mouse was sacrificed with $CO_2$ asphyxiation and the implant removed aseptically. Using sterile technique, the mesh was carefully opened and the contents filtered using a 40 micron cell strainer. (Becton Dickinson Labware, Franklin Lakes, N.J.). Cells were then collected, spun-down and counted and re-suspended in EGM-2 (Clonetics, Walkersville, Md.). Cells were plated onto cell chambers slides (Lab-Tek* II Chamber Slide System, Nunc, Rochester, N.Y.) pre-coated with 5 ng/ml fibronectin (Calbiochem, La Jolla, Calif.) at a density of $2 \times 10^4$ or $4 \times 10^4$ per $cm^2$. Cells were allowed to adhere over 24 hours and then processed for CD133 staining as described above.

Figure 21:
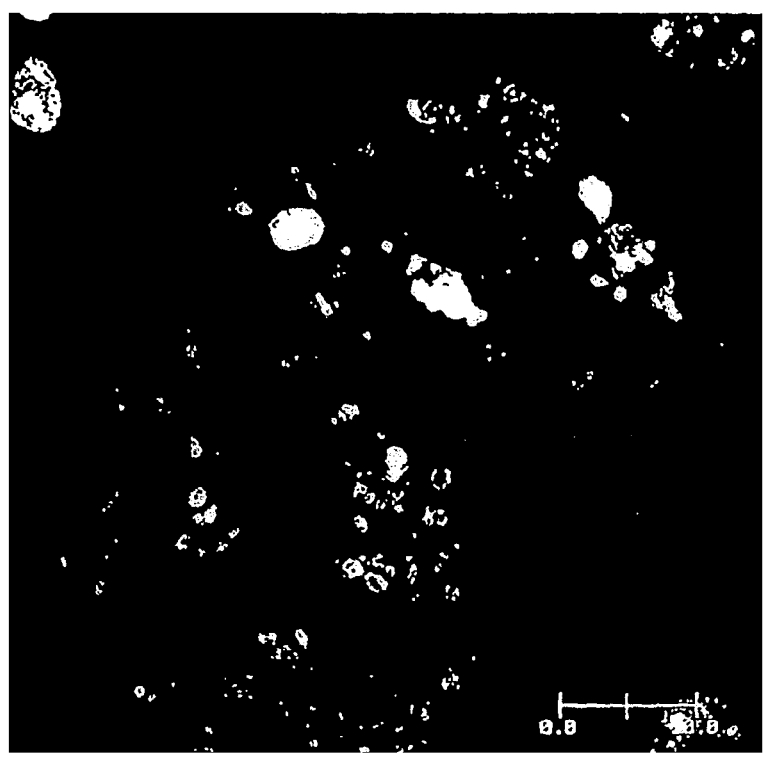
FIG. 21 shows a confocal scanning laser image of explanted cells from a 1 week VEGF/GM-CSF implant after 1 day of culture ex vivo. Cells staining positive for CD133 (red) are located in two major clusters (white arrows) although CD133 positive cells can be found throughout the section. Cells also stained positive for an antibody to β-galactosidase (data not shown). Nuclei are counterstained in dapi (blue). (Magnification 120×. Scale bar is in microns.)

Results:

Approximately 5×10⁵ progenitor cells were collected from the initial processing of the implant. Further trypsinization of cells and the implant itself 24 hours later resulted in another 5×10⁵ collected for a total of approximately 1 million progenitor cells per implant. Approximately 30-40% of cells plated staining positive for CD133 (FIG. 21). The CD133⁺ cells have a rounded morphology and are about 2-5 microns in diameter.

Conclusions:

Viable CD133⁺ progenitor cells can be collected from subcutaneously placed implants.

REFERENCES

1. Mathiowitz, E., J. Jacob, Y. Jong, G. Carino, D. Chickering, P. Chaturvedi, C. Santos, K. Vijayaraghavan, S. Montgomery, M. Bassett, and C. Morrell, Biologically erodable microspheres as potential oral drug delivery systems. Nature, 1997. 386: p. 410-414.
2. Sandor, M., S. Mehta, J. Harris, C. Thanos, P. Weston, J. Marshall, and E. Mathiowitz, Transfection of HEK cells via DNA-loaded PLGA and P(FASA) nanospheres. J Drug Target, 2002. 10(6): p. 497-506.
3. Sandor, M., D. Enscore, P. Weston, and E. Mathiowitz, Effect of protein molecular weight on release from micron-sized PLGA microspheres. J Control Release, 2001. 76(3): p. 297-311.
4. Kreitz, M. R., Controlled release of heparin from small-diameter, microporous vascular grafts, in Artificial Organs, Biomaterials and Cellular Technology. 1999, Brown University: Providence. p. 200.
5. Kreitz, M. R., J. A. Domm, and E. Mathiowitz, Controlled delivery of therapeutics from microporous membranes: II: In vitro degradation and release of heparinloaded poly(D,L-lactide-co-glycolide) microspheres. Biomaterials, 1997. 18: p. 1645-1651.
6. Kreitz, M. R., W. L. Webber, P. M. Galletti, and E. Mathiowitz, Controlled delivery of therapeutics from microporous membranes: I: Fabrication and characterization of microporous polyurethane membranes containing polymer microspheres. Biomaterials, 1997. 18: p. 597-603.
7. Rafii, S, and D. Lyden, Therapeutic stem and progenitor cell transplantation for organ vascularization and regeneration. Nat Med, 2003. 9(6): p. 702-12.
8. Hill, H., T. J. Conway, M. Sabel, Y. Jong, E. Mathiowitz, R. Bankert, and N. Egilmez, Cancer immunotherapy with interleukin 12 and granulocyte-macrophage colonystimulating factor-encapsulated microspheres: coinduction of innate and adaptive antitumor immunity and cure of disseminated disease. Cancer Res., 2002. 62(24): p. 7254-63.
9. Egilmez, N., Y. Jong, S. Hess, J. Jacob, E. Mathiowitz, and R. Bankert, Cytokines delivered by biodegradable microspheres promote effective suppression of human tumors by human peripheral blood lymphocytes in the SCID-Winn model. J. Immunother, 2000. 23(2): p. 190-5.
10. Murohara, T., H. Ikeda, J. Duan, S. Shintani, K. Sasaki, H. Eguchi, I. Onitsuka, K. Matsui, and T. Imaizumi, Transplanted cord blood-derived endothelial precursor cells augment postnatal neovascularization. J Clin Invest, 2000. 105(11): p. 1527-36.
11. Kalka, C., H. Masuda, T. Takahashi, W. M. Kalka-Moll, M. Silver, M. Kearney, T. Li, J. Isner, and t. Asahara, Transplantation of ex vivo explanded endothelial progenitor cells for therapeutic neovascularization. PNAS, 2000. 97(7): p. 3422-3427.
12. Shi, Q., S. Rafii, M. Wu, E. Wijelath, C. Yu, A. Ishida, Y. Fujita, S. Kothari, R. Mohle, L. Sauvage, M. Moore, R. Storb, and W. Hammond, Evidence for circulating bone marrow-derived endothelial cells. Blood, 1998. 92(2): p. 362-7.
13. Rafii, S., M. Oz, J. Seldomridge, B. Ferris, A. Asch, R. Nachman, F. Shapiro, E. Rose, and H. Levin, Characterization of hematopoietic cells arising on the textured surface of left ventricular assist devices. Ann Thorac Surg, 1995. 60(6): p. 1627-32.
14. Tateishi-Yuyama, E., H. Matsubara, T. Murohara, U. Ikeda, S. Shintani, H. Masaki, K. Amano, Y. Kishimoto, K. Yoshimoto, H. Akashi, K. Shimada, T. Iwasaka, and T. Imaizumi, Therapeutic Angiogenesis using Cell Transplantation (TACT) Study Investigators. Therapeutic angiogenesis for patients with limb ischaemia by autologous transplantation of bone-marrow cells: a pilot study and a randomized controlled trial. Lancet, 2002. 360(9331): p. 427-35.
15. Edelberg, J., L. Tang, K. Hattori, D. Lyden, and S. Rafii, Young adult bone marrowderived endothelial precursor cells restore aging-impaired cardiac angiogenic function. Circ Res, 2002. 90(10): p. E89-93.
16. Heissig, B., K. Hattori, S. Dias, M. Friedrich, B. Ferris, N. Hackett, R. Crystal, P. Besmer, D. Lyden, M. Moore, Z. Werb, and S. Rafii, Recruitment of stem and progenitor cells from the bone marrow niche requires MMP-9 mediated release of kit-ligand. Cell, 2002. 109(5): p. 625-37.
17. Young, P., A. Hofling, and M. Sands, VEGF increases engraftment of bone marrowderived endothelial progenitor cells (EPCs) into vasculature of newborn murine recipients. Proc Natl Acad Sci, 2002. 99(18): p. 11951-6.
18. Murayama, T., O. Tepper, M. Silver, H. Ma, D. Losordo, J. Isner, T. Asahara, and C. Kalka, Determination of bone marrow-derived endothelial progenitor cell significance in angiogenic growth factor-induced neovascularization in vivo. Exp. Hematol, 2002. 30(8): p. 967-72.
19. Lyden, D., K. Hattori, S. Dias, C. Costa, P. Blaikie, L. Butros, A. Chadburn, B. Heissig, W. Marks, L. Witte, Y. Wu, D. Hicklin, Z. Zhu, N. Hackett, R. Crystal, M. Moore, K. Hajjar, K. Manova, R. Benezra, and S. Rafii, Impaired recruitment of bone marrowderived endothelial and hematopoietic precursor cells blocks tumor angiogenesis and growth. Nature and Medicine, 2001. 7: p. 1194-1201.
20. Rafii, S., B. Heissig, and K. Hattori, Efficient mobilization and recruitment of marrow-derived endothelial and hematopoietic stem cells by adenoviral vectors expressing angiogenic factors. Gene Therapy, 2002. 9: p. 631-641.
21. Hattori, K., S. Dias, B. Heissig, N. R. Hackett, D. Lyden, M. Tateno, D. J. Hicklin, Z. Zhu, L. Witte, R. G. Crystal, M. A. S. Moore, and S. Rafii, Vascular Endothelial Growth Factor and Angiopoietin-1 Stimulate Postnatal Hematopoiesis by Recruitment of Vasculogenic and Hematopoietic Stem Cells. Journal of Experimental Medicine, 2001. 193(9): p. 1005-1014.
22. Asahara, T., T. Murohara, A. Sullivan, M. Silver, R. van der Zee, T. Li, B. Witzenbichler, G. Schatteman, and J. Isner, Isolation of Putative Progenitor Endothelial Cells for Angiogenesis. Science, 1997. 275(5302): p. 964-7.
23. Asahara, T., T. Takahashi, H. Masuda, C. Kalka, D. Chen, H. Iwaguro, Y. Inai, M. Silver, and J. Isner, VEGF contributes to postnatal neovascularization by mobilizing bone marrow-derived endothelial progenitor cells. EMBO, 1999. 18(14): p. 3964-3972.
24. Kalka, C., H. Masuda, T. Takahashi, R. Gordon, O. Tepper, E. Gravereaux, A. Pieczek, H. Iwaguro, S. Hayashi, J. Isner, and T. Asahara, Vascular endothelial growth factor 25. Luttun, A., G. Carmeliet, and P. Carmeliet, Vascular progenitors: from biology to treatment. Trends Cardiovasc Med, 2002. 12(2): p. 88-96.
26. Bautz, F., S. Rafii, L. Kanz, and R. Mohle, Expression and secretion of vascular endothelial growth factor-A by cytokine-stimulated hematopoietic progenitor cells. Possible role in the hematopoietic microenvironment. Exp Hematol, 2000. 28(6): p. 700-6.
27. Takahashi, T., C. Kalka, H. Masuda, D. Chen, M. Silver, M. Kearney, M. Magner, J. M. Isner, and T. Asahara, Ischemia- and cytokine-induced mobilization of bone marrow-derived endothelial progenitor cells for neovascularization. Nature Medicine, 1999. 5(4): p. 434-438.
28. Kalka, C., et al., Vascular endothelial growth factor(165) gene transfer augments circulating endothelial progenitor cells in human subjects. Circ Res, 2000. 86(12): p. 1198-202.

Equivalents

The foregoing written specification is to be considered to be sufficient to enable one skilled in the art to practice the invention. The particular antibodies and peptides disclosed herein are not to be construed as limiting of the invention as they are intended merely as illustrative of particular embodiments of the invention as enabled herein. Therefore, any peptides, antibodies, and antibody fragments that are functionally equivalent to those described herein are within the spirit and scope of the claims appended hereto. Indeed, various modifications of the invention in addition to those shown and described herein will become apparent to those skilled in the art from the foregoing description and fall within the scope of the appended claims.

All references, patents and patent publications that are recited in this application are incorporated in their entirety herein by reference.

What is claimed is:

1. A method of recruiting progenitor cells to a site in the body of a subject comprising:
    introducing at the site in the body of the subject an implant comprising
    an external porous housing having pores of a size sufficient to allow movement into the implant of the progenitor cells to be recruited, wherein the pores have a size ranging from about 15 to about 20 microns, and
    a drug delivery system contained within the housing, wherein the drug delivery system comprises a plurality of particles, wherein the particles are electrostatic and aggregate, have a diameter ranging from 10 nanometers to 10 microns and wherein at least two different cytokines that recruit progenitor cells are encapsulated in the particles in an effective amount to recruit progenitor cells, wherein the cytokines are not physically attached to the drug delivery system, and
    wherein the housing is a non-degradable mesh, and wherein the housing is sealed, and
    allowing sufficient time for the progenitor cells to migrate to and enter the implant.
2. The method of claim 1, wherein the external porous housing is a polymeric mesh.
3. The method of claim 2, wherein the polymeric mesh is composed of nylon.
4. The method of claim 1, wherein the cytokines are selected from the group consisting of VEGF-A, VEGF-B, VEGF-C, VEGF-D, VEGF-E, aFGF, bFGF, angiopoietin-1, angiopoietin-2, angiogenin, Del-1, follistatin, HGF/SF, leptin, midkine, PLGF, PD-ECGF, PDGF-BB, PTN, progranulin, proliferin, TGF-alpha, TGF-beta, TNF-alpha, IGF-1, IGF-2, GM-CSF, G-SCF, SDF-1a, SDF-1b, MCP-1, stem cell factor/kit ligand, M-CSF, IL-8, SF20 and HCC-1.
5. The method of claim 4, wherein the cytokines are GM-CSF and VEGF.
6. The method of claim 1, wherein the progenitor cells are selected from endothelial progenitor cells, hematopoietic progenitor cells, hemangioblasts, neural progenitor cells, and epithelial progenitor cells.
7. The method of claim 6, wherein the hematopoietic progenitor cells are CD133+ or CD34+ cells.
8. An implant for recruiting progenitor cells to a site in the body of a subject comprising
    an external porous housing having pores of a size sufficient to allow movement into the implant of the progenitor cells to be recruited, wherein the pores have a size ranging from about 15 to about 20 microns, and
    a drug delivery system contained within the housing, wherein the drug delivery system comprises a plurality of particles, wherein the particles are electrostatic and aggregate, have a diameter ranging from 10 nanometers to 10 microns and wherein at least two different cytokines that recruit progenitor cells are encapsulated in the particles in an effective amount to recruit progenitor cells, and
    wherein the cytokines are not physically attached to the drug delivery system, and
    wherein the housing is a non-degradable mesh, and wherein the housing is sealed.
9. The implant of claim 8, wherein the external porous housing is a polymeric mesh.
10. The implant of claim 9, wherein the polymeric mesh is composed of nylon.
11. The implant of claim 8, wherein the cytokines are GM-CSF and VEGF.
12. The implant of claim 8, wherein the progenitor cells are selected from endothelial progenitor cells, hematopoietic progenitor cells, hemangioblasts, neural progenitor cells, and epithelial progenitor cells.
13. The implant of claim 12, wherein the hematopoietic progenitor cells are CD133+ or CD34+ cells.
14. The method of claim 1, further comprising removing the implant from the subject and isolating the progenitor cells.
15. The implant of claim 8, further comprising one or more factors selected from the group consisting of growth factors, angiogenic/vasculogenic factors and bone marrow recruiting factors.
16. The implant of claim 8, wherein the cytokines are selected from the group consisting of VEGF-A, VEGF-B, VEGF-C, VEGF-D, VEGF-E, aFGF, bFGF, angiopoietin-1, angiopoietin-2, angiogenin, Del-1, follistatin, HGF/SF, leptin, midkine, PLGF, PD-ECGF, PDGF-BB, PTN, progranulin, proliferin, TGF-alpha, TGF-beta, TNF-alpha, IGF-1, IGF-2, GM-CSF, G-SCF, SDF-1a, SDF-1b, MCP-1, stem cell factor/kit ligand, M-CSF, IL-8, SF20 and HCC-1.
17. The implant of claim 8, wherein the particles comprise one or more biodegradable polymers.
18. The implant of claim 8, wherein the cytokines comprise at least one angiogenic/vasculogenic factor and at least one bone marrow recruiting factor.
19. The implant of claim 8, wherein the cytokines are released in vivo from the particles in a controlled or sustained manner.
20. The implant of claim 19, wherein the cytokines are released for at least 7 days in vivo.

* * * * *

UNITED STATES PATENT AND TRADEMARK OFFICE
CERTIFICATE OF CORRECTION

| | | |
|---|---|---|
| PATENT NO. | : 8,486,438 B2 | Page 1 of 1 |
| APPLICATION NO. | : 10/587884 | |
| DATED | : July 16, 2013 | |
| INVENTOR(S) | : Mathiowitz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,651 days.

Signed and Sealed this
Eleventh Day of November, 2014

Michelle K. Lee
*Deputy Director of the United States Patent and Trademark Office*